(12) United States Patent
Zawadzka et al.

(10) Patent No.: US 8,841,453 B2
(45) Date of Patent: Sep. 23, 2014

(54) HYBRID CHOLINESTERASE INHIBITORS

(71) Applicants: Uniwersytet Warszawski, Warsaw (PL); Centrum Medyczne Ksztalcenia Podyplomowego, Warsaw (PL)

(72) Inventors: Anna Zawadzka, Warsaw (PL); Zbigniew Czarnocki, Warsaw (PL); Iwona Lozinska, Legionowo (PL); Zuzanna Moleda, Warsaw (PL); Miroslawa Panasiewicz, Warsaw (PL)

(73) Assignees: Uniwersytet Warszawski, Warsaw (PL); Centrum Medyczne Ksztalcenia Podyplomowego, Warsaw (PL)

( * ) Notice: Subject to any disclaimer, the term of this patent is extended or adjusted under 35 U.S.C. 154(b) by 0 days.

(21) Appl. No.: 14/087,744

(22) Filed: Nov. 22, 2013

(65) Prior Publication Data

US 2014/0080860 A1 Mar. 20, 2014

Related U.S. Application Data

(63) Continuation-in-part of application No. PCT/PL2012/000038, filed on May 29, 2012.

(30) Foreign Application Priority Data

Jun. 3, 2011 (PL) .......................................... 395113
Apr. 4, 2012 (PL) .......................................... 398731

(51) Int. Cl.
*C07D 401/12* (2006.01)
*C07D 487/04* (2006.01)
*C07D 209/16* (2006.01)
*A61K 31/4353* (2006.01)
*C07D 209/14* (2006.01)
*A61K 31/435* (2006.01)

(52) U.S. Cl.
CPC ............ *C07D 209/14* (2013.01); *C07D 209/16* (2013.01); *C07D 487/04* (2013.01); *A61K 31/435* (2013.01); *C07D 401/12* (2013.01)
USPC .............................. 546/106; 546/79; 514/297

(58) Field of Classification Search
CPC .. C07D 487/04; C07D 209/14; C07D 401/12; A61K 31/435
USPC ....................................... 546/106, 79; 514/297
See application file for complete search history.

(56) References Cited

FOREIGN PATENT DOCUMENTS

WO WO 2005/005413 1/2005

OTHER PUBLICATIONS

Pilar Munoz-Ruiz et al al 2005, Design, Synthesis, and Biological evaluation of Dual Binding Site Acetylcholinesterase Inhibitors: New Disease-modifying agents for Alzheimers Disease.*
Maria Isabel Rodriguez-Franco, et al., Novel Tacrine-Melatonin Hybrids as Dual-Acting Drugs for Alzheimer Disease, With Improved Acetylcholinesterase Inhibitory and Antioxidant Properties, J. Med. Chem. (2006) vol. 49, p. 459-462.
Aleksandra Siwicka, et al., The Oxidation Products of Melatonin Derivatives Exhibit Acetylcholinesterase and Butyrylcholinesterase Inhibitory Activity, J. Pineal Research (2008) vol. 55, No. 1 p. 40-49.

* cited by examiner

*Primary Examiner* — Rita Desai
(74) *Attorney, Agent, or Firm* — VedderPrice, P.C.; Thomas J. Kowalski; Deborah L. Lu

(57) ABSTRACT

The invention relates to novel hybrid cholinesterase inhibitors containing the melatonin or its oxidation products unit and tetrahydroacridine unit linked via a carbamate bond. Due to the high selectivity of action, which is expressed with high ratio of $IC_{50}$ for acetylcholinesterase inhibition to $IC_{50}$ for butyrylcholinesterase inhibition ($[IC_{50}(AChE)]/[IC_{50}(BChE)]$), the novel compounds may be used in relief and/or treatment of the neurodegenerative diseases, among them the Alzheimer's disease.

7 Claims, 1 Drawing Sheet

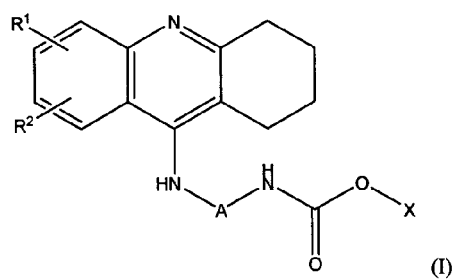
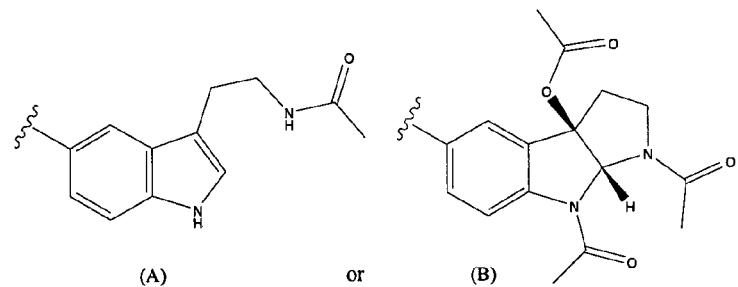
X=

HYBRID CHOLINESTERASE INHIBITORS

This application is a continuation-in-part application of international patent application Serial No. PCT/PL2012/000038 filed May 29, 2012, which published as PCT Publication No. WO 2012/165981 on Dec. 6, 2012, which claims benefit of Polish patent application Serial Nos. P-395113 and P-398731, filed Jun. 3, 2011 and Apr. 4, 2012, respectively.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to novel hybrid cholinesterase inhibitors, which may contain the melatonin or its oxidation products unit and tetrahydroacridine unit linked via a carbamate bond can be used in relief and/or treatment of the neurodegenerative diseases, among them the Alzheimer's disease.

BACKGROUND OF THE INVENTION

Alzheimer's disease (AD) is the most common type of dementia in the elderly. In the 1990s, about 15 million people suffered from AD (Hebert L. E., Scherr P. A., Beckett L. A. et al.; *J. Am. Med. Assoc.* 1995, 273, 1354-1359), and WHO estimates that if current trends persist, this number will double by 2020 (Dufouil C., Alperovitch A.; *Rev. Prat.* 2005, 55, 1869-1878). The disease symptoms are cognitive and behavioral dysfunctions and progressive memory loss.

Despite very intensive research, there is no effective causal therapy of AD so far, and the treatment focuses only on the relief of symptoms. One of the leading therapeutic strategies is based on the assumption that increasing the amount of the neurotransmitter acetylcholine, leads to a better use of the cholinergic neurons, which in turn slows down the progression of the disease. This objective can be achieved by inhibition of acetylcholinesterase (Bartus R. T., Dean R. L., Beer B. et al.; *Science* 1982, 217, 408-417). Recently, it became clear that butyrylocholinesterase also participates in the control of neurotransmission. In a healthy brain acetylocholinesterase accounts for 80% of the total cholinesteric activity. In case of people suffering from AD, its activity drops to about 60% of the initial value, while increasing the role of butyrylcholinesterase (Greig N. H., Utsuki T., Yu Q. S.; *Curr. Med. Res. Opin.* 2001, 17, 159-165). It seems therefore, that a strategy aimed at inhibiting the activity of butyrylcholinesterase or both enzymes simultaneously can produce much better therapeutic effects.

The characteristic changes in the brain of AD patients are β-amyloid plaques and neurofibrillary tangles, accompanied by neurodegeneration. Also, large quantities of cholinesterases, in particular butyrylcholinesterase, can be found in both β-amyloid plaques and neurofibrillary tangles (Guillozet A. L., Smiley J. F., Mash D. C. et al.; *Ann. Neurol.* 1997, 42, 909-918). Therefore cholinesterases may be involved in the formation of plaques and tangles and additionally enhance their toxicity, activating the microglia and hydrolyzing acetylcholine (Greig N. H., Utsuki T., Yu Q. S.; *Curr. Med. Res. Opin.* 2001, 17, 159-165).

It thus appears that the inhibition of cholinesterases can not only improve the functioning of damaged cholinergic system, but can also prevent its further degeneration.

The compounds used so far in symptomatic treatment of the Alzheimer's disease are tacrine, withdrawn from the market due to serious side effects, and later less toxic compounds of the same mechanism of action, among them donepezil, rivastigmine and galanthamine. These compounds differ in the specifity of action; donepezil inhibits only acetylcholinesterase while rivastigmine acts against both enzymes, exhibiting thus a higher efficiency.

In the last ten years, the research of the new cholinesterase inhibitors expanded to include a group called hybrid drugs—compounds combining in their structures two fragments, a known drug and its copy or two different drugs. These hybrid structures exhibit much higher activity compared to their 'non-hybrid' precursors, often showing a synergistic effect of the action.

The publication of the international patent application WO 2004/032929 discloses compounds containing in their structure the tetrahydroacridine ring, acting as dual site acetylcholinesterase inhibitors, especially useful in treatment of cognitive disorders as senile dementia, cerebrovascular dementia, mild cognition impairment, attention deficit disorder, and/or neurodegenerative dementing disease with aberrant protein aggregations as specially Alzheimer's disease, Parkinson disease, ALS, or prion diseases, as Creutzfeldt-Jakob disease or Gerstmann-Straussler-Scheinher disease. Among the compounds disclosed, there are structures containing tetrahydroacridine ring, of which the amine group is connected with the benzene ring of indanone or indanodione through an alkyl linker, possibly containing amine or amide groups.

Oxidative stress is another important factor involved in the neurodegenerative diseases. Therefore, use of the compounds exhibiting antioxidative properties can have a beneficial effect (Floyd R. A., Hensley K., *Neurobiol. Aging* 2002, 23, 795-807). One of the important antioxidants of well documented activity is the endogenous melatonin (Reiter R. J. et al, *Acta. Biochim. Pol.* 2003, 50, 1129-1146).

The conception of combining the melatonin (N-acetyl-5-methoxytryptamine) and tetrahydroacridine units was explored in the works of Rodriguez-Franco M. I. and coworkers (*J. Med. Chem.* 2006, 49, 459-462 and *Chem. Med. Chem.* 2009, 4, 828-841), who developed hybrid compounds containing amide linkage. These compounds, which are 2-(1H-indol-3-yl)ethyl esters of [(1,2,3,4-tetrahydroacridin-9-ylamino)alkyl]-carbamate acid, disclosed also in the publication of the international patent application WO 2005/005413, exhibit the activity towards inhibition of cholinesterases and additionally have antioxidant properties and prevent the Aβ (β-amyloid) aggregation, therefore acting as neuroprotectors.

Authors of the present invention demonstrated in their previous works (Siwicka A., Moleda Z., Wojtasiewicz K., Zawadzka A., Maurin J. K., Panasiewicz M., Pacuszka T., Czarnocki Z.; *J. Pineal Research* 2008, 45, 40-49 and Mole da Z., Wojtasiewicz K., Panasiewicz M., Czarnocki Z.; *J. Pineal Research* 2010, 49, 55-59) that the phenyl- and alkyl-carbamate derivatives of melatonin and products of its oxidation with singlet oxygen exhibit cholinesterase inhibitory activity.

Citation or identification of any document in this application is not an admission that such document is available as prior art to the present invention.

DETAILED DESCRIPTION

The idea of using the method of substitution of melatonin and its oxidation products via a carbamate bond involving the phenolic oxygen atom has led the Applicants of this invention to obtain new compounds. These compounds exhibit a much higher cholinesterase inhibitory activity than previously described derivatives containing melatonin or its oxidation products units or compounds in which melatonin and tetrahydroacridine units are connected via a linker containing an amide bond.

The present invention provides the inhibitors of cholinesterase of the hybrid structure presented by the general formula (I)

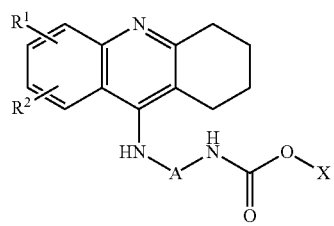

(I)

wherein:
A represents straight or branched $C_2$-$C_{14}$-alkyl group,
$R^1$, $R^2$ are the same or different and they are independently selected from hydrogen, halogen, $C_1$-$C_3$-alkyl, $C_1$-$C_3$-alkyl substituted by halogen atoms and $C_1$-$C_3$-alkoxy,
X represents a radical of formula (A) or (B)

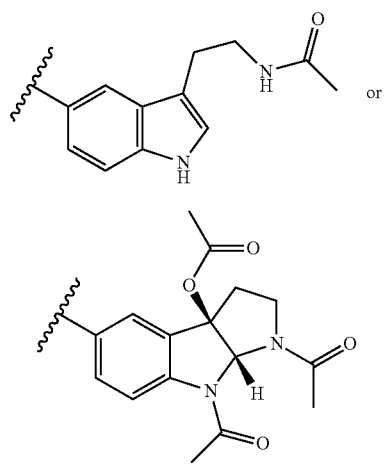

(A)

or (B)

and the pharmaceutically acceptable salts thereof.

Compounds of the general formula (I) according to the invention show inhibiting activity towards cholinesterase, and also have antioxidant properties and prevent aggregation of Aβ (β-amyloid), therefore can be potential neuroprotective drugs.

Therefore, the invention also provides the use of compounds of the general formula (I), for preparation of medicines for prevention and/or treatment of the neurodegenerative disorders like: senile dementia, vascular dementia, mild cognitive impairment, attention deficit disorder, neurodegenerative dementia with abnormal protein aggregation, in particular Alzheimer's disease, Parkinson's disease, ALS or prion diseases like Creutzfeldt-Jakob disease, and Gerstmann-Sträussler-Scheinker disease in the diagnosed patients.

Although one can consider the per se administration of compounds of general formula (I), they will generally be used in the form of pharmaceutical formulation, appropriate for each case route of drug administration.

Another aspect of the invention is therefore the pharmaceutical formulation containing the active compound of formula (I), in which X, A, $R^1$ and $R^2$ have the meaning defined above, in therapeutically effective amount.

Another aspect of the invention is the method of treatment of a patient, that comprise a drug administration in accordance with individual needs of such treatment with therapeutically effective amount of a compound of general formula (I), in which X, A, $R^1$ and $R^2$ have the meaning defined above or its pharmaceutical formulation or its unit dosage form.

The invention provides also a process for the preparation of cholinesterase inhibitors of the general formula (I),

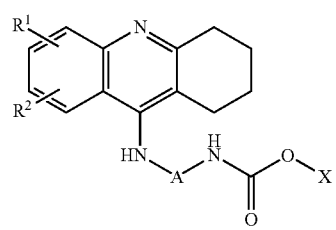

(I)

wherein:
A represents straight or branched $C_2$-$C_{14}$-alkyl group,
$R^1$, $R^2$ are the same or different and they are independently selected from hydrogen, halogen, $C_1$-$C_3$-alkyl, $C_1$-$C_3$-alkyl substituted by halogen atoms and $C_1$-$C_3$-alkoxy,
X represents a radical of formula (A) or (B)

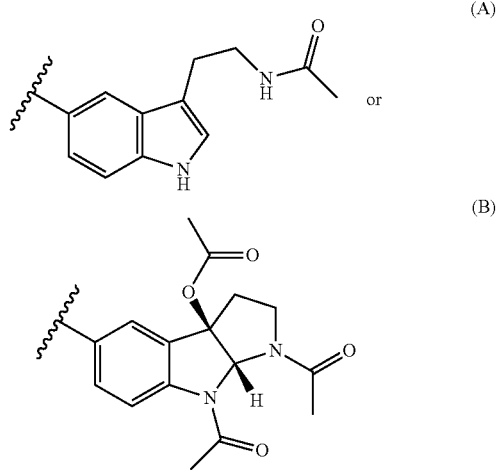

(A)

or (B)

The process involves obtaining desired products from amine derivatives of 1,2,3,4-tetrahydroacridine of formula (III),

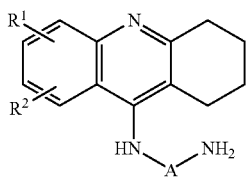

wherein:

A, $R^1$ and $R^2$ have the same meaning as in general formula (I).

The compounds of formula (I) may be obtained by reaction of N-acylation of the amino derivative of tetrahydroacridine of formula (III) with an active ester derivative of melatonin or its oxidation product, preferably 4-nitrophenyl carbonate derivative of formula (II),

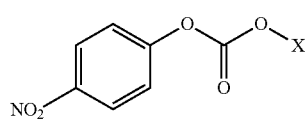

wherein X has the same meaning as in formula (I).

The 4-nitrophenyl carbonate derivatives of formula (II), wherein X represents a radical of formula (A) or (B) are new compounds and they are also encompassed by this invention.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1 depicts a general formula of cholinesterase inhibitors wherein:

A represents straight or branched $C_2$-$C_{14}$-alkyl group, $R^1$, $R^2$ are the same or different and they are independently selected from hydrogen, halogen, $C_1$-$C_3$-alkyl, $C_1$-$C_3$-alkyl substituted by halogen atoms and $C_1$-$C_3$-alkoxy, X represents a radical of formula (A) or (B).

DETAILED DESCRIPTION OF THE INVENTION

The term "$C_2$-$C_{14}$ alkyl group" used herein refers to a straight or branched hydrocarbon chain containing no unsaturated bonds, having 2 to 14 carbon atoms.

The term "halogen" refers to chemical elements from 17 (formerly VIIA or VII main) group of the Periodic Table fluorine, chlorine, bromine and iodine.

The "$C_1$-$C_3$-alkyl group" refers to alkyl group comprising from 1 to 3 carbon atoms.

The "$C_1$-$C_3$-alkoxy group" refers to alkyl group comprising from 1 to 3 carbon atoms connected to tetrahydroacridine ring by oxygen atom.

One of the preferred group of compounds according to the invention are those of formula (I), in which X is represented by group (A), A is $C_2$-$C_{14}$-alkyl, and both $R^1$ and $R^2$ are hydrogen atoms. In this case compounds are represented by following formula (IA):

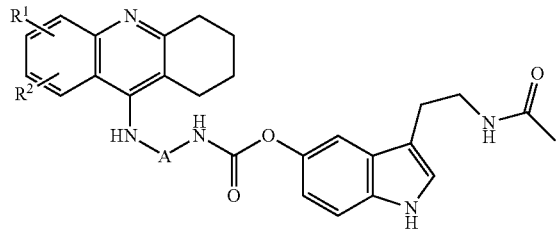

Another preferred group of compounds according to the invention are those of formula (IA), in which X is represented by group (A), A is $C_2$-$C_{14}$-alkyl, $R^1$ represents a halogen atom substituted at position 6 or 7 of 1,2,3,4-tetrahydroacridine ring, and $R^2$ represents a hydrogen atom.

Even more preferred group of compounds according the invention are those of the formula (IA), in which X is represented by group (A), A is $C_2$-$C_{14}$-alkyl, $R^1$ represents a chlorine atom substituted at position 6 or 7 of 1,2,3,4-tetrahydroacridine ring, and $R^2$ represents a hydrogen atom.

Another preferred group of compounds of the invention are those of the formula (I), in which X is represented by group (B), A is $C_2$-$C_{14}$-alkyl, both $R^1$ and $R^2$ are hydrogen atoms. In this case compounds are represented by following formula (IB):

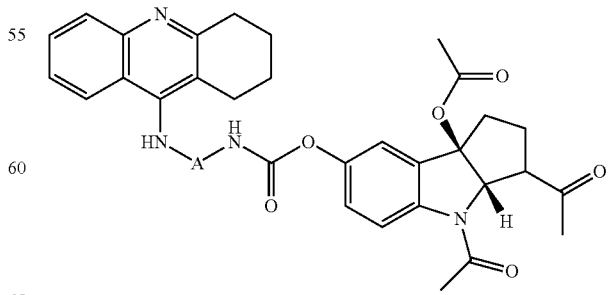

Particularly preferred compounds of the invention are selected from the group comprising:

(a) 3-[2-(acetylamino)ethyl]-1H-indol-5-yl[7-(1,2,3,4-tetrahydroacridin-9-ylamino)heptyl]carbamate,
(b) 3-[2-(acetylamino)ethyl]-1H-indol-5-yl[2-(1,2,3,4-tetrahydroacridin-9-ylamino)ethyl]carbamate,
(c) 3-[2-(acetylamino)ethyl]-1H-indol-5-yl[6-(1,2,3,4-tetrahydroacridin-9-ylamino)hexyl]carbamate,
(d) 3-[2-(acetylamino)ethyl]-1H-indol-5-yl{7-[(6-chloro-1,2,3,4-tetrahydroacridin-9-yl)amino]heptyl}carbamate,
(e) 3-[2-(acetylamino)ethyl]-1H-indol-5-yl{2-[(6-chloro-1,2,3,4-tetrahydroacridin-9-yl)amino]ethyl}carbamate,
(f) 1,8-diacetyl-5-({[7-(1,2,3,4-tetrahydroacridin-9-ylamino)heptyl]carbamoyl}oxy)-2,3,8,8a-tetrahydropyrrolo[2,3-b]indol-3a(1H)-yl acetate,
(g) 1,8-diacetyl-5-({[6-(1,2,3,4-tetrahydroacridin-9-ylamino)hexyl]carbamoyl}oxy)-2,3,8,8a-tetrahydropyrrolo[2,3-b]indol-3a(1H)-yl acetate,
(h) 3-[2-(acetylamino)ethyl]-1H-indol-5-yl[3-(1,2,3,4-tetrahydroacridin-9-ylamino)propyl]carbamate,
(i) 3-[2-(acetylamino)ethyl]-1H-indol-5-yl[4-(1,2,3,4-tetrahydroacridin-9-ylamino)butyl]carbamate,
(j) 3-[2-(acetylamino)ethyl]-1H-indol-5-yl[5-(1,2,3,4-tetrahydroacridin-9-ylamino)pentyl]carbamate,
(k) 3-[2-(acetylamino)ethyl]-1H-indol-5-yl[8-(1,2,3,4-tetrahydroacridin-9-ylamino)octyl]carbamate,
(l) 3-[2-(acetylamino)ethyl]-1H-indol-5-yl{7-[(7-chloro-1,2,3,4-tetrahydroacridin-9-yl)amino]heptyl}carbamate,
(m) 3-[2-(acetylamino)ethyl]-1H-indol-5-yl{2-[(7-chloro-1,2,3,4-tetrahydroacridin-9-yl)amino]ethyl}carbamate,
(n) 3-[2-(acetylamino)ethyl]-1H-indol-5-yl[10-(1,2,3,4-tetrahydroacridin-9-ylamino)decyl]carbamate,
(o) 3-[2-(acetylamino)ethyl]-1H-indol-5-yl[12-(1,2,3,4-tetrahydroacridin-9-ylamino)dodecyl]carbamate,
(p) 3-[2-(acetylamino)ethyl]-1H-indol-5-yl{10-[(7-chloro-1,2,3,4-tetrahydroacridin-9-yl)amino]decyl}carbamate,
(q) 3-[2-(acetylamino)ethyl]-1H-indol-5-yl{12-[(7-chloro-1,2,3,4-tetrahydroacridin-9-yl)amino]dodecyl}carbamate,
(r) 3-[2-(acetylamino)ethyl]-1H-indol-5-yl{10-[(6-chloro-1,2,3,4-tetrahydroacridin-9-yl)amino]decyl}carbamate,
(s) 3-[2-(acetylamino)ethyl]-1H-indol-5-yl{12-[(6-chloro-1,2,3,4-tetrahydroacridin-9-yl)amino]dodecyl}carbamate.

Compounds of the formula (I) wherein X represents a radical of formula (A) or (B) can be obtained by reaction of N-acylation of the amino derivative of tetrahydroacridine of formula (III) with an active ester derivative of melatonin or its oxidation product, preferably 4-nitrophenyl carbonate derivative of formula (II), in which X has the same meaning as in formula (I), as shown below in Scheme 1.

SCHEME 1

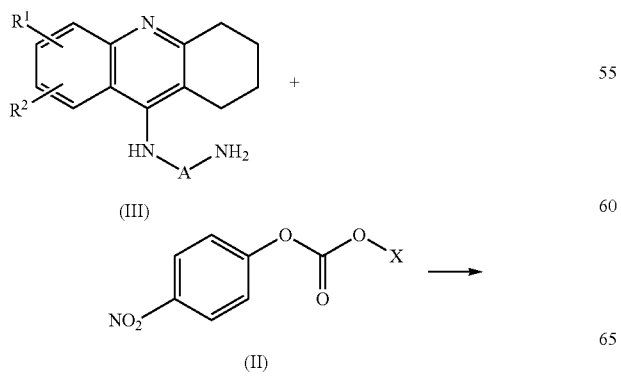

(III)

(II)

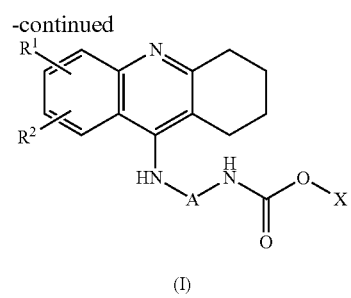

(I)

The starting compounds for the synthesis of compounds of formula (I) can be prepared by known methods described in the literature for this type of derivatives.

The starting compounds derivatives of tetrahydroacridine of formula (III) can be obtained by methods described in literature Recanatini M. et al. *J. Med. Chem.* 2000, 43, 2007-2018 and Carlier, P. R. et al. *J. Med. Chem.* 1999, 42, 4225-4231, according to Scheme 2. In the first step the selected 2-aminobenzonitrile is condensed with cyclohexanone in the presence of POCl$_3$, and then the resulting derivative of 9-chloro-1,2,3,4-tetrahydroacridine is reacted with diamine of formula H$_2$N-A-NH$_2$, in which A is C$_2$-C$_{14}$-alkyl.

SCHEME 2

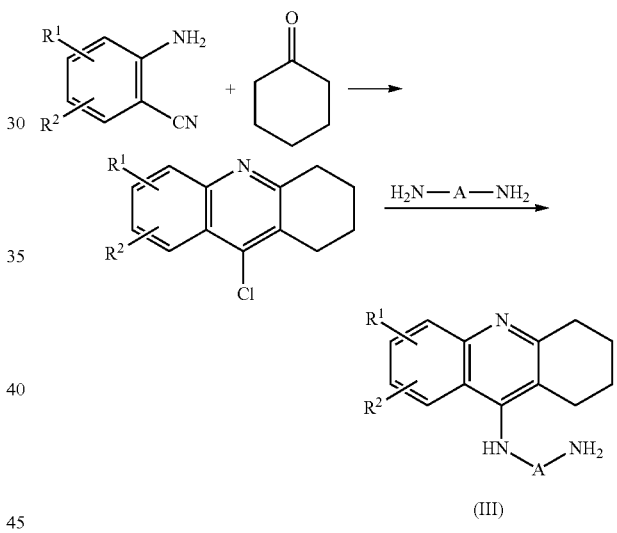

(III)

The active esters of formula (II), in which X represents a radical of formula (A) or (B),

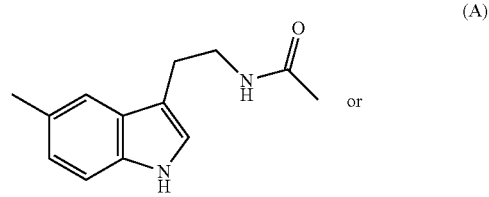

(A)

or

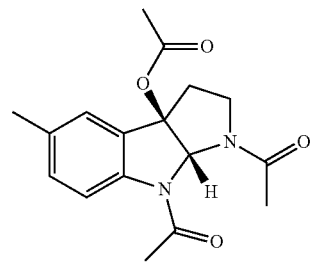

(B)

can be obtained, for example, in the reaction of 4-nitrophenyl chloroformate with hydroxy-derivatives of formula (IV) representing respectively precursors of compounds of formula (IIA) or (IIB), in the presence of a base such as N-methylmorpholine, in an aprotic solvent such as tetrahydrofuran, according to Scheme 3.

SCHEME 3

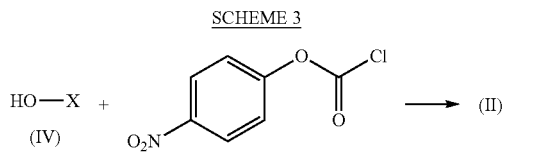

The starting compounds of formula (II) are obtained by estrification of 4-nitrophenyl chloroformate with hydroxy-derivatives of melatonin or its oxidation products of formula (IVA) and (IVB), respectively:

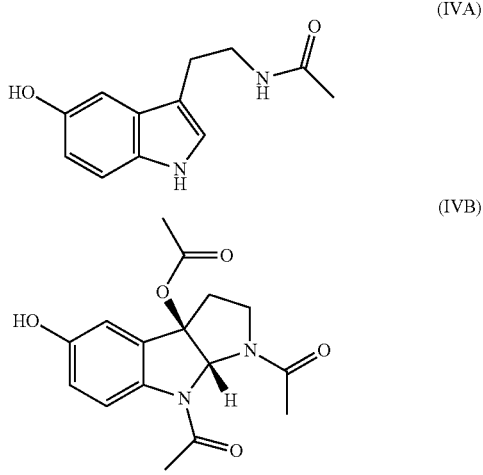

Hydroxy-derivatives of melatonin of formula (IVA) and (IVB) can be prepared in accordance with the procedure described in publications: *J. Pineal Research* 2008, 45, 40-49 and *J. Pineal Research* 2010, 49, 55-59. Compound of formula (IVA), N-acetylserotonin, may be obtained by selective N-acetylation of serotonin. The oxidation products of melatonin of formula (IVB) are prepared by singlet oxygen-induced cyclization of derivative (IVA), after the protection of a hydroxyl function by tert-butyldimethylsilyl (TBDMS) group. The cyclization reaction is preferably carried out in methanol with the addition of pyridine at −78° C. in the presence of tetraphenyloporphirine—the oxidation catalyst. The oxidation product is then acetylated with boiling acetic anhydride in the presence of p-toluenesulphonic acid, followed by removing of protecting group using tetrabutylammonium fluoride in tetrahydrofuran.

Compounds of the general formula (I) may be present in the racemic form, as well as pure enantiomers or/and mixture thereof. All optical isomers of the compounds according to the invention and the mixtures thereof are covered by the present claims. Enantiomers as well as their racemic mixtures may be prepared according to the methods well-known in the art by means of chromatographic resolution methods, including chiral HPLC, but also kinetic enzymatic resolution methods, chemical resolution method involving salt formation (also addition salts) or may be synthesized with the use of the appropriate chiral auxiliaries or adjuvants or by the stereoselective synthesis.

Compounds of the general formula (I) may form pharmaceutically acceptable salts (addition salts) with acids. The term "pharmaceutically acceptable salts" refers to the salts with inorganic or organic acids that are allowed in a medical treatment of humans. Examples of these acids are as follows: hydrochloric, hydrobromic, sulfuric, nitric, phosphoric, fumaric, maleinic, glycolic, lactic, adipinic, ascorbic, salicylic, succinic, tartaric, acetic, formic, benzoic, citric, malonic, malic, p-toluenosulfonic, methanesulfonic, naphthalenosulfonic, and benzenosulfonic. Other acids like oxalic acid may be useful as intermediate salts in the preparation process of the compounds covered by this invention.

Hydrochloride salts of compounds (I) are particularly useful.

As stated above, compounds of the general formula (I) may be administered in the human treatment alone or in the combination with other pharmacologically active compounds in the therapeutically effective doses in the prevention and/or treatment of the neurodegenerative disorders like: senile dementia, vascular dementia, mild cognitive impairment, attention deficit disorder, neurodegenerative dementia with abnormal protein aggregation, in particular Alzheimer's disease, Parkinson's disease, ALS or prion diseases like Creutzfeldt-Jakob disease, and Gerstmann-Strässler-Scheinker disease in the diagnosed patients.

The term "treatment" used herein means the inhibition of the state, disorder or disease, namely prevention, delay or reduction of the development of the disease, or of the recurrence of the disease or at least one of its clinical symptoms, or a complete cure of the disease, which is the removal of the state, disorder or disease or at least one of its clinical symptoms.

The term "therapeutically effective amount" used herein relates to the amount of the compound that upon the administration to the patient for the purpose of treatment status, condition or disease is sufficient to affect the treatment. The "therapeutically effective amount" will be different depending on the given compound and also on the mode or the way of administration, the medical condition and its severity, and also depending on the age, weight, physical condition and sensitivity of the patient, and it may be established by the clinicist on the basis of his knowledge and clinical tests.

The therapeutically effective daily amount of the compound of the formula (I) may be administrated to the patient as a single unit dose once daily or divided into several daily doses in determined time intervals. A less frequent than daily administration may be accomplished when the active compound is in a prolonged-release formulation or in the depot form.

The pharmaceutical formulations, in addition to the active substance, may contain known pharmaceutically acceptable carriers and/or excipients appropriate for a given pharmaceutical form, devoted of their own pharmacological activity and adverse reactions with the active substance.

The pharmaceutical formulation may be formulated in the pharmaceutical dosage form suitable for administration by any route, for example orally, intranasal, rectally, topically (including buccally and sublingually), parenterally (including intramuscular, intravenous, subcutaneous), or by inhalation. The selection and the amount of carriers and excipients depends on the form and route of administration of the pharmaceutical formulation. The appropriate dosage form may be formulated with the use of methods and techniques well known to those skilled in the art, including combining the active compound with one or more liquid or solid carriers and/or excipients.

The pharmaceutical formulation suitable for oral administration may be prepared in the form of tablets, capsules, starch capsules, film-coated tablets, enteric-coated tablets, and also in the form of powder or granules, as well as in the liquid form. Tablets or capsules for oral administration may contain excipients such as binders, fillers, wetting agents, disintegrators, and lubricants. The liquid pharmaceutical formulation may be present in the form of water or oil suspensions, solutions, emulsions, syrups or elixirs, and also may be prepared from powder or granules by dissolution thereof in water or any suitable solvent prior to administration. The liquid pharmaceutical formulations may contain any traditional auxiliary agents like dispersing or emulsifying agents, non-aqueous carriers like edible oils, and preservatives.

A pharmaceutical preparation for oral administration may be in the form of capsules. In this case, the active substance is combined with a carrier and gelatin capsules are filled with the obtained composition. Capsules may be soft and hard gelatin capsules, differing by composition of gelatin shell for its preparation. Gelatin shell in case of soft capsules include plastisizers, such as glycerol, sorbitol; preservatives, such as benzoic acid and its salts, alkyl hydroxybenzoates; colourants and flavourings. Capsule filling is in the form of oil solution, suspension or emulsion. Appropriate carriers include, for example castor, coconut, olive, palm, corn, peanut oil, synthetic and natural triglycerides of fatty acids, unsaturated medium-chain fatty acids, modified long-chain fatty acids, glycol esters, polyethylene glycols and others. Appropriate excipients are tensides, for example lecithine, mono- and diglycerides and polyoxyethylene sorbitan fatty acid esters.

Pharmaceutical formulation for parenteral administration may be in the form of suspension ready to use, lyophilisate form for reconstitution ex tempore or a concentrate for preparation of intravenous infusions. Carriers appropriate for intravenous pharmaceutical formulations include, for example, sterile aqueous solutions, such as saline solution, carbohydrate solution, for example glucose, mannitol, dextrose lactose and aqueous solutions of buffers, for example phosphate buffer. Moreover, the agent may contain other excipients, conventionally used in order to ensure osmolarity, antioxidants, preservatives and others.

The pharmaceutical formulation for parenteral administration (including intramuscular, subcutaneous and intravenous) may be in the form of suspension ready to use, lyophilisate form for reconstitution ex tempore or a concentrate for preparation of intravenous infusions. Such formulations may be present as a single-dose ampoules, pre-filled syringes, small volume infusion or in multidose containers with preservative added and may include carriers, suspending agents, stabilizers and/or dispersing agents. Carriers suitable for administration of intravenous pharmaceutical formulation include, for example, sterile aqueous solutions such as saline solution, solutions of carbohydrates, such as glucose, mannitol, dextrose, lactose or aqueous buffers, such as phosphate buffer. The product also may contain other auxiliary substances, commonly used to ensure isoosmoticity, antioxidants, preservatives and others. Alternatively, the active ingredient may be in the solid form, obtained by preparing the powder in sterile aseptic conditions or by lyophilization from a solution, to be used with a suitable sterile vehicle, like water free from pyrogenic substances.

For topical administration on the skin, the compounds of the invention may be prepared in the form of ointments, creams or lotions, including those especially formulated for transdermal use. Transdermal formulations may contain substances which enable the permeation, such as linalool, carvacrol, thymol, citral, menthol, or anethole. Ointments and creams may, for example, be water-based or in a form of oil solution with the addition of suitable thickening and/or gelling agents. Lotions may also be made based on an aqueous or oil suspensions, and usually also contain one or more emulsifiers, stabilizers, dispersing agents, suspending, thickening or colouring additives.

The compounds of the invention may also be administered as a liquid nasal sprays or powders or dispersed in the form of drops. Drops can be made on an aqueous or non-aqueous basis, further comprising one or more dispersing agents, solubilizers or suspending agents. The compounds may also be administered by inhalation from the inhalation device, nebulizer or a pressurized container or by any other means to provide an aerosol spray. The inhaling device may be equipped with a control valve capable of delivering a pre-measured amount of active substance. The inhaling device may contain a propellant, such as dichlorodifluoromethane, trichlorofluoromethane, dichlorotetrafluoroethane, carbon dioxide, nitrogen or other suitable gas. Alternatively, for delivery by inhalation or insufflations, the compounds of the invention may be in the form of a dry powder, for example, a powdered mixture of the particulate compound and a suitable carrier such as lactose or starch. Powder compositions may be presented in unit dosage forms, for example in capsules or cartridges, gelatine or blister packs from which the powder may be administered using an inhaler or any other inhalation device.

The biological activity of the compounds of general formula (I) towards the cholinesterase inhibition was evaluated using Ellman's method (Ellman, G. L.; Courtney, K. D.; Anders, B.; Featherstone, R. M. *Biochem. Pharmacol.* 1961, 7, 88-95).

This method of evaluation of the cholinesterase inhibitors activity is based on the fact that acetyl/butyrylcholinesterase interacts with the inhibitor, which prevents the acetyl/butyrylcholine hydrolysis. The inhibitor causes the enzyme activity drop which is dependent on the inhibitor concentration. The enzyme unbound with the inhibitor is able to hydrolyze acetyl/butyrylthiocholine (ASCh/BSCh). The amount of the hydrolyzed ASCh/BSCh is measured indirectly, by quantification of the product of its reaction with DTNB (5,5'-dithio-bis-2-nitrobenzoic acid). Ellman's method relies therefore on the spectrophotometric quantification of product of the reaction between acylthiocholine and DTNB. $IC_{50}$ value corresponds to the inhibitor concentration which causes the 50% decrease of the enzyme activity.

The enzymes are derived from human blood: AChE from the erythrocytes and BChE from the plasma. The phosphate buffer of pH 8.0 is used as the reference compound (lack of inhibition; enzyme activity—100%).

The results of the biological evaluation are presented in Table 1.

TABLE 1

| | Compound | | |
|---|---|---|---|
| example no. | $IC_{50}$ AChE [nM] | $IC_{50}$ BChE [nM] | Selectivity $IC_{50}(AChE)/IC_{50}(BChE)$ |
| 1 | 33.77 ± 2.74 | 0.25 ± 0.02 | 135.1 |
| 2 | 1096.67 ± 25.25 | 4.28 ± 1.93 | 256.2 |
| 3 | 178.38 ± 16.29 | 2.04 ± 0.22 | 87.4 |
| 4 | 7.7 ± 0.73 | 0.38 ± 0.07 | 20.3 |
| 5 | 20.05 ± 5.82 | 34.5 ± 7.55 | 0.6 |
| 7 | 36.81 ± 2.87 | 3.15 ± 0.83 | 11.7 |
| 8 | 269.68 ± 19.40 | 58.17 ± 9.62 | 4.6 |
| 9 | 377.54 ± 42.36 | 15.49 ± 2.84 | 24.4 |
| 10 | 186.44 ± 11.18 | 2.07 ± 0.5 | 90.1 |
| 11 | 4.61 ± 0.32 | 0.25 ± 0.03 | 18.4 |
| 12 | 39.88 ± 9.19 | 0.88 ± 0.06 | 45.3 |

TABLE 1-continued

| example no. | IC$_{50}$ AChE [nM] | IC$_{50}$ BChE [nM] | Selectivity IC$_{50}$(AChE)/ IC$_{50}$(BChE) |
|---|---|---|---|
| 13 | 3280.6 ± 451.45 | 8.20 ± 0.78 | 400.1 |
| 14 | 1.18 ± 0.12 | 0.28 ± 0.04 | 4.2 |
| 15 | 3.8 ± 0.16 | 0.24 ± 0.08 | 15.8 |
| 16 | 1.43 ± 0.02 | 1.64 ± 0.14 | 0.9 |
| 17 | 7.00 ± 0.72 | 0.78 ± 0.16 | 9 |
| 18 | 8.10 ± 0.70 | 1.20 ± 0.16 | 6.7 |
| 19 | 25.60 ± 1.30 | 1.31 ± 0.04 | 19.5 |

The compounds according to the invention exhibit a much higher biological activity against cholinesterases, especially butyrylcholinesterase, than the compounds described in the prior art. The IC$_{50}$ values of the derivatives containing melatonin and tacrine units reported in the literature (Rodrigues-Franco M. I. et al; Chem Med Chem 2009, 4, 828-841 and Rodrigues-Franco M. I. et al; J. Med. Chem. 2006, 49, 459-462) are from 0.008 nM to 40 nM for the inhibition of AChE and from 2.5 nM to 175 nM for the inhibition of BChE. The compounds according to the invention demonstrate high selectivity of action, which is expressed with high ratio of IC$_{50}$ for acetylcholinesterase inhibition to IC$_{50}$ for butyrylcholinesterase inhibition ([IC$_{50}$(AChE)]/[IC$_{50}$(BChE)]).

The results presented above clearly show that the novel compounds of the formula (I), containing the melatonin or its oxidation products unit and tetrahydroacridine unit linked with a carbamate bond, exhibit inhibitory activity against cholinesterases and can be used as potential drugs in prevention and/or treatment of the neurodegenerative disorders.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

3-[2-(acetylamino)ethyl]-1H-indol-5-yl[7-(1,2,3,4-tetrahydroacridin-9-ylamino)heptyl]carbamate

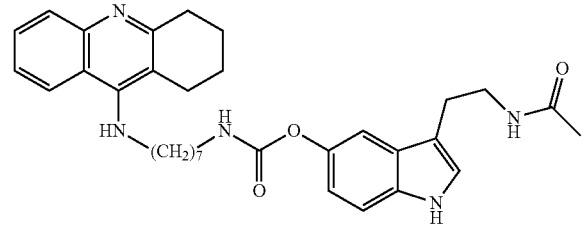

A. 3-[2-(acetylamino)ethyl]-1H-indol-5-yl 4-nitrophenyl carbonate

To N-acetylserotonin (0.9 g; 4 mmol) was added N-methylmorpholine (0.92 ml, 8 mmol), and 4-nitrophenyl chloroformate (1.61 g; 8 mmol) dissolved in tetrahydrofuran. Reaction was carried out for 0.5 h under an argon atmosphere. The solvent was evaporated. The residue was purified by column chromatography (SiO$_2$, methanol/methylene chloride) to give 0.92 g (yield 60%) of crystalline yellow product with a melting point 153-156° C.

$^1$H NMR (200 MHz, CDCl$_3$), δ (ppm): 9.34 (br.s, 1H, NH), 8.28 (m, 2H, H$_{arom}$), 7.48 (m, 2H, H$_{arom}$), 7.36 (m, 2H, H$_{arom}$), 7.07 (m, 2H, H$_{arom}$), 5.72 (br.s, 1H, NH), 3.55 (m, 2H, CH$_2$), 2.92 (m, 2H, CH$_2$), 1.93 (s, 3H, COCH$_3$); $^{13}$C NMR (50 MHz, CDCl$_3$), δ (ppm): 170.61, 155.66, 152.23, 145.67, 144.60, 134.73, 127.85, 125.56, 124.20, 121.99, 115.39, 113.57, 112.19, 110.46, 40.09, 25.39, 23.52; MS EI(+)(m/z): 406 [M+Na]$^+$; HR MS EI(+)(m/z): calculated for C$_{19}$H$_{17}$N$_3$O$_6$Na ([M+Na]$^+$) 406.1015. found 406.1010.

B. 3-[2-(acetylamino)ethyl]-1H-indol-5-yl[7-(1,2,3,4-tetrahydroacridin-9-ylamino)heptyl]carbamate To the tacrine derivative of formula (III), where R$_1$, R$_2$=H, A=(CH$_2$)$_7$ (100 mg, 0.32 mmol) dissolved in tetrahydrofuran were added 39.2 mg (0.35 mmol) of 4-dimethylaminopyridine (DMAP) and then 61 mg (0.16 mmol) of active ester of formula (IIA) dissolved in tetrahydrofuran, which was obtained as described in step A. Reaction was carried out for 1 h under argon. Product was purified by column chromatography (SiO$_2$, diethyl ether/chloroform/methanol) to give 9.8 mg (yield 11%) of the title compound as an oil.

$^1$H NMR (500 MHz, CDCl$_3$), δ (ppm): 8.56 (s, 1H), 7.96 (d, J=7.5 Hz, 1H), 7.90 (d, J=8.5 Hz, 1H), 7.54 (m, 1H), 7.34 (dt, J$_1$=1.0 Hz, J$_2$=8.5 Hz, 1H), 7.27 (s, 1H), 7.24 (d, J=8.5 Hz, 1H), 6.96 (s, 1H), 6.91 (dd, J$_1$=2.0 Hz, J$_2$=8.5 Hz, 1H), 5.69 (s, 1H), 5.11 (t, J=5.8 Hz, 1H), 3.98 (br. s, 1H, NH), 3.49 (m, 4H), 3.25 (td, J$_1$=7.0 Hz, J$_2$=13.5 Hz, 2H), 3.06 (s, 2H), 2.86 (t, J=6.8 Hz, 2H), 2.71 (s, 2H), 1.91 (m, 4H), 1.90 (s, 3H), 1.66 (m, 2H), 1.54 (m, 2H), 1.36 (m, 6H); $^{13}$C NMR (125 MHz, CDCl$_3$), δ (ppm): 170.23, 158.49, 155.77, 150.80, 147.48, 144.47, 134.11, 128.69, 128.31, 127.68, 123.63, 123.39, 122.87, 120.27, 116.58, 115.95, 113.14, 111.56, 111.02, 49.44, 41.18, 39.80, 34.03, 31.68, 29.78, 28.95, 26.81, 26.58, 25.18, 24.81, 23.33, 23.06, 22.79; MS EI(+)(m/z): 556 [M+H]$^+$; HR MS EI(+)(m/z): calculated for C$_{33}$H$_{42}$N$_5$O$_3$ ([M+H]$^+$) 556.3288. found 556.3279.

Example 2

3-[2-(acetylamino)ethyl]-1H-indol-5-yl[2-(1,2,3,4-tetrahydroacridin-9-ylamino)ethyl]carbamate

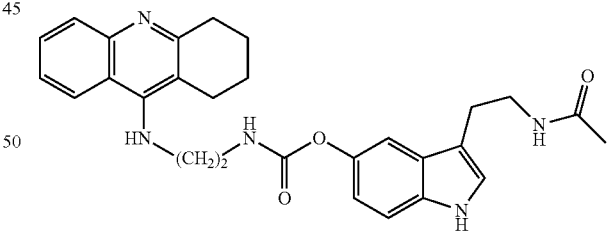

Following the same procedure as in the Example 1, but starting from compound III, where R$_1$, R$_2$=H, A=(CH$_2$)$_2$ (170 mg; 0.7 mmol), the 51 mg of the title compound was obtained with the yield of 30%.

$^1$H NMR (500 MHz, CD$_3$OD), δ (ppm): 8.13 (d, J=8.5 Hz, 1H), 7.78 (dd, J$_1$=8.5 Hz, J$_2$=0.5 Hz, 1H), 7.56 (td, J$_1$=7.0 Hz, J$_2$=1.5 Hz, 1H), 7.37 (td, J$_1$=8.0 Hz, J$_1$=1.0 Hz, 1H), 7.27 (d, J=8.5 Hz, 1H), 7.19 (d, J=2.5 Hz, 1H), 7.10 (s, 1H), 6.73 (dd, J$_1$=8.5 Hz, J$_2$=2.0 Hz, 1H), 3.72 (t, J=6.0 Hz, 2H), 3.45-3.40 (m, 4H), 2.98 (t, J=6.0 Hz, 2H), 2.88 (t, J=7.5 Hz, 2H), 2.78 (t, J=6.0 Hz, 2H), 1.91-1.88 (m, 4H), 189 (s, 3H); $^{13}$C NMR (125 MHz, CD$_3$OD), δ (ppm): 173.25, 159.17, 158.96, 153.15, 147.75, 145.37, 135.82, 129.86, 128.95, 127.85, 125.01, 125.01, 124.34, 121.28, 117.21, 116.80, 113.64, 112.46, 111.64, 49.85, 42.86, 41.49, 34.13, 26.16, 26.13, 24.08, 23.62, 22.61; MS EI(+)(m/z): 486 [M+H]⁺; HR MS EI(+)(m/z): calculated for $C_{28}H_{32}N_5O_3$ ([M+H]⁺) 486.2505. found 486.2509.

3-[2-(acetylamino)ethyl]-1H-indol-5-yl[2-(1,2,3,4-tetrahydroacridin-9-ylamino)ethyl]carbamate hydrochloride m.p. 163-166° C.

Example 3

3-[2-(acetylamino)ethyl]-1H-indol-5-yl[6-(1,2,3,4-tetrahydroacridin-9-ylamino)hexyl]carbamate

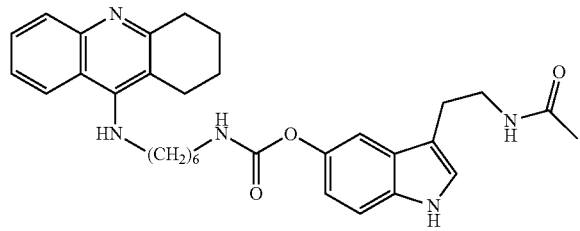

Following the same procedure as in the Example 1, but starting from compound III, where $R_1$, $R_2$=H, A=$(CH_2)_6$ (174 mg, 0.58 mmola), the 25 mg of the title compound was obtained with the yield of 16%.

¹H NMR (500 MHz, CD₃OD), δ (ppm): 8.13 (d, J=8.5 Hz, 1H), 7.76 (dd, J₁=8.5 Hz, J₂=0.5 Hz, 1H), 7.57 (td, J₁=6.5 Hz, J₂=1.0 Hz, 1H), 7.38 (td, J₁=8.5 Hz, J₂=1.5 Hz, 1H), 7.27 (dd, J₁=8.5 Hz, 0.5 Hz, 1H), 7.23 (dd, J₁=2.0 Hz, J₂=0.5 Hz, 1H), 7.10 (s, 1H), 6.80 (dd, J₁=8.5 Hz, J₂=2.0 Hz, 1H), 3.59 (t, J=6.0 Hz, 2H), 3.14 (t, J=7.5 Hz, 2H), 3.16 (t, J=7.0 Hz, 2H), 2.97 (t, J=6.5 Hz, 2H), 2.87 (t, J=7.0 Hz, 2H), 2.73 (t, J=5.5 Hz, 2H), 1.92-1.85 (m, 4H), 1.89 (s, 3H), 1.72-1.67 (m, 2H), 1.57-1.52 (m, 2H), 1.43-1.38 (m, 4H); ¹³C NMR (125 MHz, CD₃OD), δ (ppm): 173.41, 158.72, 158.35, 154.01, 147.10, 145.68, 135.92, 130.41, 129.14, 127.13, 125.07, 125.07, 124.83, 120.96, 117.05, 116.51, 113.80, 112.57, 111.83, 49.74, 41.89, 41.71, 33.74, 32.31, 30.91, 27.67, 27.60, 26.28, 26.12, 24.11, 23.62, 22.76; MS EI(+)(m/z): 543 [M+H]⁺; HR MS EI(+)(m/z): calculated for $C_{32}H_{40}N_5O_3$ ([M+H]⁺) 542.3131. found 542.3137.

Example 4

3-[2-(acetylamino)ethyl]-1H-indol-5-yl{7-[(6-chloro-1,2,3,4-tetrahydroacridin-9-yl)amino]heptyl}carbamate

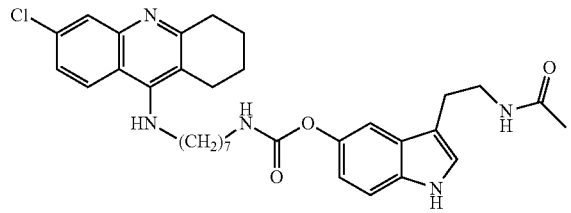

Following the same procedure as in the Example 1, but starting from compound III, where $R_1$=6-Cl, $R_2$=H, A=$(CH_2)_7$ (270 mg, 0.78 mmola), the 165 mg of the title compound was obtained with the yield of 72%.

¹H NMR (500 MHz, CDCl₃), δ (ppm): 8.89 (s, 1H), 7.89 (d, J=7.0 Hz, 1H), 7.88 (s, 1H), 7.23 (m, 3H), 6.89 (s, 1H), 6.87 (d, J=2.0 Hz, 1H), 5.85 (t, J=5.5 Hz, 1H), 5.28 (t, J=5.5 Hz, 1H), 4.06 (br.s, 1H), 3.45 (m, 4H), 3.24 (m, 2H), 3.01 (s, 2H), 2.81 (t, J=6.5 Hz, 2H), 2.64 (s, 2H), 1.88 (s, 7H), 1.65 (m, 2H), 1.55 (m, 2H), 1.36 (s, 6H); ¹³C NMR (125 MHz, CDCl₃), δ(ppm): 170.47, 159.40, 156.04, 151.12, 149.53, 147.95, 144.45, 134.25, 127.74, 127.30, 124.82, 124.36, 123.61, 118.39, 116.50, 115.75, 113.00, 111.72, 111.03, 49.57, 41.26, 39.93, 33.92, 31.72, 29.87, 28.99, 26.85, 26.65, 25.25, 24.64, 23.38, 22.98, 22.67; MS EI(+)(m/z): 590 [M+H]⁺; HR MS EI(+)(m/z): calculated for $C_{33}H_{41}ClN_5O_3$ ([M+H]⁺) 590.2898. found 590.2894.

Example 5

3-[2-(acetylamino)ethyl]-1H-indol-5-yl{2-[(6-chloro-1,2,3,4-tetrahydroacridin-9-yl)amino]ethyl}carbamate

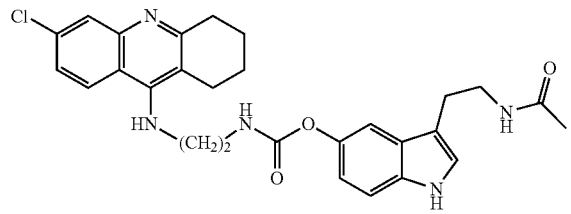

Following the same procedure as in the Example 1, but starting from compound III, where $R_1$=6-Cl, $R_2$=H, A=$(CH_2)_2$ (100 mg, 0.36 mmola), the 65 mg of the title compound was obtained with the yield of 70%.

¹H NMR (200 MHz, CD₃OD), δ (ppm): 8.12 (m, 1H, $H_{arom}$), 7.75 (m, 1H, $H_{arom}$), 7.32 (m, 1H, $H_{arom}$), 7.28 (m, 1H, $H_{arom}$), 7.18 (m, 1H, $H_{arom}$), 7.26 (s, 1H, $H_{arom}$), 6.70 (dd, J₁=10.0 Hz, J₂=1.9 Hz, 1H), 3.75 (t, J=6.0 Hz, 2H), 3.44 (m, 4H), 2.94 (m, 4H), 2.75 (m, 2H), 1.89 (s, 7H); ¹³C NMR (50 MHz, CD₃OD), δ (ppm): 173.24, 160.43, 158.99, 153.28, 148.44, 145.32, 135.82, 135.59, 128.94, 126.55, 126.46, 125.31, 125.01, 119.47, 117.21, 116.75, 113.63, 112.46, 111.61, 49.68, 42.86, 41.48, 34.26, 26.14, 26.10, 23.97, 23.51, 22.61; MS EI(+)(m/z): 521 [M+H]⁺; HR MS EI(+)(m/z): calculated for $C_{28}H_{31}ClN_5O_3$ ([M+H]⁺) 520.2115. found 520.2115.

Example 6

1,8-diacetyl-5-({[7-(1,2,3,4-tetrahydroacridin-9-ylamino)heptyl]carbamoyl}oxy)-2,3,8,8a-tetrahydropyrrolo[2,3-b]indol-3a(1H)-yl acetate

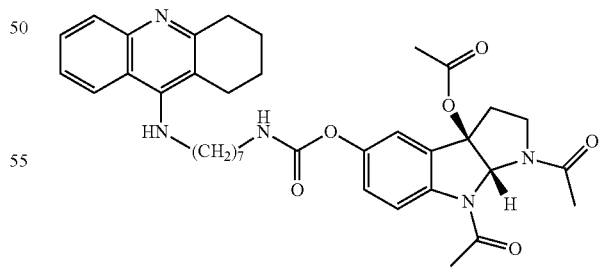

A. 1,8-diacetyl-5-{[(4-nitrophenoxy)carbonyl]oxy}-2,3,8,8a-tetrahydropyrrolo[2,3-b]indol-3a(1H)-yl acetate To the solution of 1,8-diacetyl-5-hydroxy-2,3,8,8a-tetrahydropyrrolo[2,3-b]indol-3a(1H)-yl acetate (88 mg; 0.28 mmol) in N-methylmorpholine (62 μl, 0.56 mmol) and small amount of tetrahydrofuran, the 4-nitrophenyl chloroformate (112.9 mg; 0.56 mmol) dissolved in tetrahydrofuran was added. Reaction was carried out for 3 days under an argon atmosphere. The solvent was evaporated. The residue was purified by column chromatography (SiO$_2$, cyclohexane/methylene chloride/methanol) to give 16 mg of title compound with 12% of yield.

$^1$H NMR (200 MHz, CDCl$_3$), δ(ppm): 8.33 (m, 2H, H$_{arom}$), 8.14 (m, 1H, H$_{arom}$), 7.52 (m, 2H, H$_{arom}$), 7.46 (m, 1H, H$_{arom}$), 7.28 (m, 1H, H$_{arom}$), 6.36 (s, 1H, CH), 3.77 (m, 1H), 3.14 (m, 1H), 2.90 (m, 1H), 2.62 (s, 3H, COCH$_3$), 2.43 (m, 1H), 2.10 (s, 3H, COCH$_3$), 2.05 (s, 3H, COCH$_3$); MS ESI(+) (m/z): 506 [M+Na]$^+$; HR MS EI(+)(m/z): calculated for C$_{23}$H$_{21}$N$_3$O$_9$Na ([M+Na]+) 506.1175. found 506.1163.

B. 1,8-diacetyl-5-({[7-(1,2,3,4-tetrahydroacridin-9-ylamino)heptyl]carbamoyl}oxy)-2,3,8,8a-tetrahydropyrrolo[2,3-b]indol-3a(1H)-yl acetate To the tacrine derivative of formula (III), where R$_1$, R$_2$=H, A=(CH$_2$)$_7$ (20.6 mg, 0.066 mmol) dissolved in tetrahydrofuran were added 8 mg (0.066 mmola) of 4-dimethyloaminopyridine (DMAP) and then 16 mg (0.033 mmol) of active ester of formula (IIB) dissolved in tetrahydrofuran, which was obtained as described in step A. Reaction was carried out for 23 h under argon. Product was purified by column chromatography (SiO$_2$, diethyl ether/chloroform/methanol) to give 4.3 mg (yield 20%) of the title compound.
MS ES(+)(m/z): 656 [M+H]$^+$.

Example 7

1,8-diacetyl-5-({[6-(1,2,3,4-tetrahydroacridin-9-ylamino)hexyl]carbamoyl}oxy)-2,3,8,8a-tetrahydropyrrolo[2,3-b]indol-3a(1H)-yl acetate

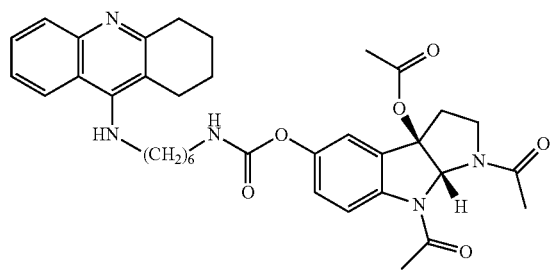

Following the same procedure as in the Example 6, but starting from compound III, where R$_1$, R$_2$=H, A=(CH$_2$)$_6$ (24 mg, 0.082 mmol), the 20.2 mg of the title compound was obtained with the yield of 78%.

$^1$H NMR (200 MHz, CDCl$_3$), δ (ppm): 8.05 (m, 1H, H$_{arom}$), 7.95 (m, 1H, H$_{arom}$), 7.52 (m, 1H, H$_{arom}$), 7.38 (m, 2H, H$_{arom}$), 7.10 (m, 1H, H$_{arom}$), 6.49 (m, 1H, H$_{arom}$), 6.32 (s, 1H), 5.14 (br. t, 1H, NH), 4.04 (br. s, 1H, NH), 3.69 (m, 1H), 3.51 (m, 2H), 3.24 (m, 2H), 3.08 (m, 2H), 3.86 (m, 1H), 2.71 (m, 2H), 2.60 (s, 3H, COCH$_3$), 2.39 (m, 2H), 2.07 (s, 3H, COCH$_3$), 2.02 (s, 3H, COCH$_3$), 1.92 (m, 4H), 1.62 (m, 4H), 1.42 (m, 4H); $^{13}$C NMR (50 MHz, CDCl$_3$), δ (ppm): 171.57, 170.37, 169.84, 158.43, 154.78, 151.05, 149.79, 141.95, 129.38, 128.66, 128.66, 124.16, 123.91, 123.02, 120.27, 119.68, 118.67, 117.11, 116.00, 90.02, 80.30, 49.51, 46.83, 41.29, 39.24, 36.09, 34.03, 31.86, 29.97, 26.76, 26.67, 24.98, 23.75, 23.22, 22.91, 21.55; HR MS EI(+)(m/z): calculated for C$_{36}$H$_{44}$N$_5$O$_6$ ([M+H]$^+$) 642.3292. found 642.3294.

Example 8

3-[2-(acetylamino)ethyl]-1H-indol-5-yl[3-(1,2,3,4-tetrahydroacridin-9-ylamino)propyl]carbamate

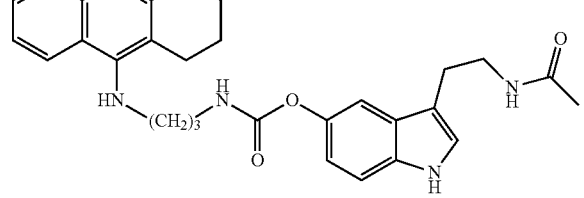

Following the same procedure as in the Example 1, but starting from compound III, where R$_1$, R$_2$=H, A=(CH$_2$)$_3$ (74 mg; 0.29 mmol), the 44.7 mg of the title compound was obtained with the yield of 60%.

$^1$H NMR (200 MHz, CDCl$_3$), δ (ppm): 8.62 (s, 1H, NH$_{indole}$), 8.00 (d, J=8.2 Hz, 1H, H$_{arom}$), 7.90 (dd, J$_1$=8.4 Hz, J$_2$=0.8 Hz, 1H, H$_{arom}$), 7.53 (m, 1H, H$_{arom}$), 7.32 (m, 1H, H$_{arom}$), 7.25 (d, J=8.8 Hz, 1H, H$_{arom}$), 7.26 (s, 1H, H$_{arom}$), 6.97 (d, J=2.5 Hz, 1H, H$_{arom}$), 6.90 (dd, J$_1$=8.8 Hz, J$_2$=2.2 Hz, 1H, H$_{arom}$), 5.83 (br. s, 1H, NHCOO), 5.43 (br. s, 1H, NHCOCH$_3$), 4.48 (br. s, 1H, NH), 3.48 (m, 7H), 3.05 (m, 2H), 2.84 (t, J=7.0 Hz, 2H), 2.72 (m, 2H), 1.91 (m, 8H); $^{13}$C NMR (50 MHz, CDCl$_3$), δ (ppm): 170.53, 158.89, 156.60, 150.54, 147.56, 144.51, 134.35, 128.87, 128.55, 127.87, 124.13, 123.68, 122.75, 120.65, 116.96, 116.65, 113.31, 111.84, 111.16, 45.96, 40.01, 38.81, 34.19, 31.85, 25.39, 25.31, 23.53, 23.24, 22.97; HR MS EI(+)(m/z): calculated for C$_{29}$H$_{34}$N$_5$O$_3$ ([M+H]$^+$) 500.2662. found 500.2659.

Example 9

3-[2-(acetylamino)ethyl]-1H-indol-5-yl[4-(1,2,3,4-tetrahydroacridin-9-ylamino)butyl]carbamate

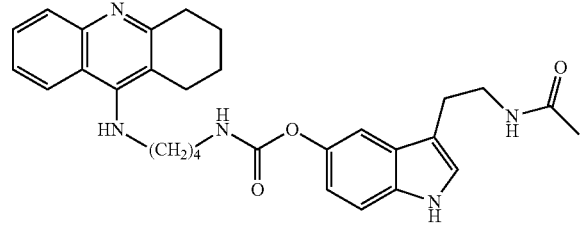

Following the same procedure as in the Example 1, but starting from compound III, where R$_1$, R$_2$=H, A=(CH$_2$)$_4$ (118 mg; 0.44 mmol), the 105 mg (yield 93%) of white crystalline product with a melting point 95-98° C. was obtained.

$^1$H NMR (200 MHz, CDCl$_3$), δ (ppm): 8.79 (s, 1H, NH$_{indole}$) 7.92 (m, 2H, H$_{arom}$), 7.54 (m, 1H, H$_{arom}$), 7.34 (m, 1H, H$_{arom}$), 7.22 (m, 2H, H$_{arom}$), 6.91 (m, 1H, H$_{arom}$), 6.87 (dd, J$_1$=8.8 Hz, J$_2$=2.2 Hz, 1H, H$_{arom}$), 5.93 (t, J=5.8 Hz, 1H, NHCOO), 5.34 (t, J=6.2 Hz, 1H, NHCOCH$_3$), 4.00 (br. s, 1H, NH), 3.46 (m, 4H), 3.28 (m, 2H), 3.05 (br. s, 2H), 2.82 (t, J=6.9 Hz, 2H), 2.70 (br. s, 2H), 1.89 (m, 7H), 1.68 (m, 4H); $^{13}$C NMR (50 MHz, CDCl$_3$), δ (ppm): 170.59, 158.80, 156.14, 150.72, 147.61, 144.46, 134.31, 128.83, 128.55, 127.82, 124.00, 123.69, 122.90, 120.54, 116.57, 116.57, 113.15, 111.81, 111.12, 49.15, 41.10, 40.01, 34.17, 29.08, 27.64, 25.34, 25.07, 23.47, 23.21, 22.94; HR MS EI(+)(m/z): calculated for C$_{30}$H$_{36}$N$_5$O$_3$ ([M+H]$^+$) 514.2818. found 514.2808.

Example 10

3-[2-(acetylamino)ethyl]-1H-indol-5-yl[5-(1,2,3,4-tetrahydroacridin-9-ylamino)pentyl]carbamate

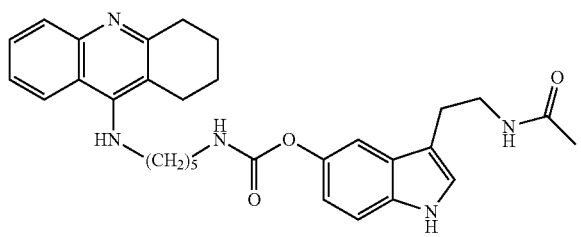

Following the same procedure as in the Example 1, but starting from compound III, where R$_1$, R$_2$=H, A=(CH$_2$)$_5$ (125 mg; 0.44 mmol), the 89.6 mg (yield 77%) of white crystalline product with a melting point 89-92° C. was obtained.

$^1$H NMR (200 MHz, CDCl$_3$), δ (ppm): 9.16 (s, 1H, NH$_{indole}$), 7.91 (m, 2H, H$_{arom}$), 7.52 (m, 1H, H$_{arom}$), 7.29 (m, 1H, H$_{arom}$), 7.20 (s, 1H, H$_{arom}$), 7.17 (d, J=8.9 Hz, 1H, H$_{arom}$), 6.80 (m, 2H, H$_{arom}$), 6.04 (t, J=5.8 Hz, 1H, NHCOO), 5.43 (t, J=6.0 Hz, 1H, NHCOCH$_3$), 4.00 (br. 1H, NH), 3.40 (m, 4H), 3.23 (m, 2H), 3.03 (br. s, 2H), 2.74 (t, J=6.9 Hz, 2H), 2.65 (br. s, 2H), 1.85 (m, 7H), 1.50 (m, 6H); $^{13}$C NMR (50 MHz, CDCl$_3$), δ (ppm): 170.67, 158.67, 156.26, 150.93, 147.53, 144.36, 134.29, 128.64, 128.51, 127.74, 123.84, 123.72, 123.04, 120.41, 116.42, 116.24, 112.88, 111.81, 111.03, 49.41, 41.11, 39.97, 34.08, 31.41, 29.83, 25.23, 24.96, 24.20, 23.36, 23.15, 22.88; HR MS EI(+)(m/z): calculated for C$_{31}$H$_{38}$N$_5$O$_3$ ([M+H]$^+$) 528.2975. found 528.2975.

Example 11

3-[2-(acetylamino)ethyl]-1H-indol-5-yl[8-(1,2,3,4-tetrahydroacridin-9-ylamino)octyl]carbamate

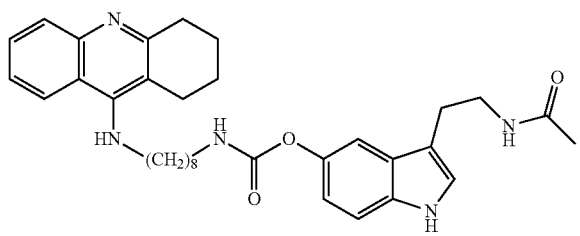

Following the same procedure as in the Example 1, but starting from compound III, where R$_1$, R$_2$=H, A=(CH$_2$)$_8$ (162 mg; 0.50 mmol), the 109 mg (yield 77%) of white crystalline product with a melting point 67-70° C. was obtained.

$^1$H NMR (200 MHz, CDCl$_3$), δ (ppm): 9.02 (br. s, 1H, NH$_{indole}$), 7.93 (m, 2H, H$_{arom}$), 7.55 (m, 1H, H$_{arom}$), 7.33 (m, 1H, H$_{arom}$), 7.22 (m, 2H, H$_{arom}$), 6.88 (m, 2H, H$_{arom}$), 5.89 (br. s, 1H, NHCOO), 5.28 (br. s, 1H, NHCOCH$_3$), 4.88 (br. s, 1H, NH), 3.45 (m, 4H), 3.23 (m, 2H), 3.05 (br. s, 2H), 2.79 (t, J=6.8 Hz, 2H), 2.69 (br. s, 2H), 1.88 (m, 7H), 1.59 (m, 4H), 1.32 (br. s, 8H); $^{13}$C NMR (50 MHz, CDCl$_3$), δ (ppm): 170.56, 158.63, 156.11, 151.03, 147.64, 144.47, 134.30, 128.75, 128.48, 127.78, 123.75, 123.70, 123.10, 120.38, 116.54, 116.01, 112.99, 111.81, 111.10, 49.62, 41.42, 39.98, 34.17, 31.92, 29.99, 29.36, 29.27, 26.97, 26.77, 25.29, 24.96, 23.43, 23.22, 22.95; HR MS EI(+)(m/z): calculated for C$_{34}$H$_{44}$N$_5$O$_3$ ([M+H]$^+$) 570.3444. found 570.3439.

Example 12

3-[2-(acetylamino)ethyl]-1H-indol-5-yl{7-[(7-chloro-1,2,3,4-tetrahydroacridin-9-yl)amino]heptyl}carbamate

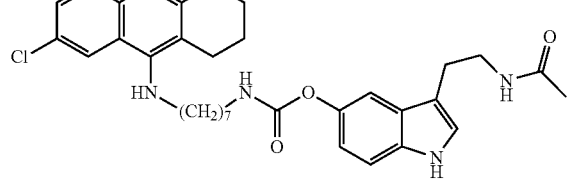

Following the same procedure as in the Example 1, but starting from compound III, where R$_1$=7-Cl, R$_2$=H, A=(CH$_2$)$_7$ (172.5 mg; 0.5 mmol), the 130.1 mg (yield 88%) of cream crystalline product with a melting point 80-82° C. was obtained.

$^1$H NMR (200 MHz, CDCl$_3$), δ (ppm): 8.82 (br. s, 1H. NH$_{indole}$), 7.94 (m, 2H, H$_{arom}$), 7.46 (m, 1H, H$_{arom}$), 7.23 (m, 2H, H$_{arom}$), 6.89 (m, 2H, H$_{arom}$), 5.84 (br. s, 1H, NHCOO), 5.23 (t, J=5.6 Hz, 1H, NHCOCH$_3$), 3.92 (br. s, 1H, NH), 3.46 (m, 4H), 3.25 (m, 2H), 3.02 (m, 2H), 2.82 (t, J=6.2 Hz, 2H), 2.68 (br. s, 2H), 1.89 (m, 7H), 1.61 (m, 4H), 1.37 (br. s, 6H); $^{13}$C NMR (50 MHz, CDCl$_3$), δ (ppm): 170.56, 159.06, 156.08, 150.24, 149.77, 146.12, 144.50, 134.29, 130.52, 129.21, 127.79, 123.65, 122.32, 121.11, 116.97, 116.61, 113.09, 111.79, 111.14, 49.58, 41.38, 39.97, 34.17, 31.85, 29.96, 29.13, 26.95, 26.78, 25.30, 24.87, 23.46, 23.08, 22.84; HR MS EI(+)(m/z): calculated for C$_{33}$H$_{40}$ClN$_5$O$_3$ ([M+H]) 590.2898. found 590.2897.

Example 13

3-[2-(acetylamino)ethyl]-1H-indol-5-yl{2-[(7-chloro-1,2,3,4-tetrahydroacridin-9-yl)amino]ethyl}carbamate

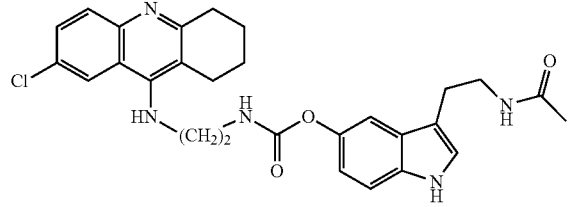

Following the same procedure as in the Example 1, but starting from compound III, where R$_1$=7-Cl, R$_2$=H, A=(CH$_2$)$_2$ (102.5 mg; 0.37 mmol), the 87.1 mg (yield 90%) of cream crystalline product with a melting point 118-123° C. was obtained.

$^1$H NMR (200 MHz, CDCl$_3$), δ (ppm): 8.45 (br. s, 1H, NH$_{indole}$), 7.89 (m, 2H, H$_{arom}$), 7.48 (m, 1H, H$_{arom}$), 7.26 (m, 2H, H$_{arom}$), 7.00 (d, J=2.2 Hz, 1H, H$_{arom}$), 6.91 (dd, J$_1$=8.8 Hz, J$_2$=2.2 Hz, 1H, H$_{arom}$), 5.83 (m, 1H, NHCOO), 5.56 (m, 1H, NHCOCH$_3$), 4.43 (m, 1H, NH), 3.65 (m, 2H), 3.51 (m, 4H), 3.01 (m, 2H), 2.87 (m, 2H), 1.89 (m, 7H), 1.79 (m, 2H); $^{13}$C NMR (50 MHz, CDCl$_3$), δ (ppm): 170.52, 159.34, 149.76, 146.09, 144.45, 138.81, 134.38, 130.68, 129.61, 129.34, 127.87, 123.70, 122.00, 121.26, 117.93, 116.64, 113.40, 111.86, 111.17, 49.62, 42.42, 39.97, 34.21, 25.44, 25.11, 23.55, 23.11, 22.85;

HR MS EI(+)(m/z): calculated for C$_{28}$H$_{30}$ClN$_5$O$_3$ ([M+H]$^+$) 520.2115. found 520.2108.

Example 14

3-[2-(acetylamino)ethyl]-1H-indol-5-yl[10-(1,2,3,4-tetrahydroacridin-9-ylamino)decyl]carbamate

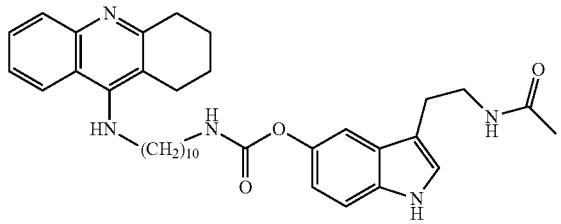

Following the same procedure as in the Example 1, but starting from compound III, where R$_1$, R$_2$=H, A=(CH$_2$)$_{10}$ (168 mg, 0.48 mmol), the 99 mg of the title compound as an oil was obtained with the yield of 70%.

$^1$H NMR (200 MHz, CDCl$_3$), δ (ppm): 9.05 (br. s, 1H, NH$_{indole}$), 7.93 (m, 2H, H$_{arom}$), 7.53 (m, 1H, H$_{arom}$), 7.33 (m, 1H, H$_{arom}$), 7.22 (m, 2H, H$_{arom}$), 6.88 (m, 2H, H$_{arom}$), 5.91 (br. s, 1H, NHCOO), 5.30 (br. s, 1H, NHCOCH$_3$), 4.03 (br. s, 1H, NH), 3.45 (m, 4H), 3.25 (m, 2H), 3.05 (br. s, 2H), 2.79 (t, J=6.6 Hz, 2H), 2.69 (br. s, 2H), 1.90 (m, 7H), 1.60 (m, 4H), 1.29 (br. s, 12H); $^{13}$C NMR (50 MHz, CDCl$_3$), δ (ppm): 170.60, 158.42, 156.13, 151.14, 147.41, 144.43, 134.29, 128.56, 128.52, 127.75, 123.74, 123.74, 123.15, 120.25, 116.50, 115.81, 112.94, 111.81, 111.09, 49.65, 41.45, 39.97, 33.99, 31.91, 30.00, 29.54, 29.51, 29.44, 29.34, 27.02, 26.87, 25.27, 24.91, 23.41, 23.19, 22.89; HR MS EI(+)(m/z): calculated for C$_{36}$H$_{48}$N$_5$O$_3$ ([M+H]$^+$) 598.3757. found 598.3773.

Example 15

3-[2-(acetylamino)ethyl]-1H-indol-5-yl[12-(1,2,3,4-tetrahydroacridin-9-ylamino)dodecyl]carbamate

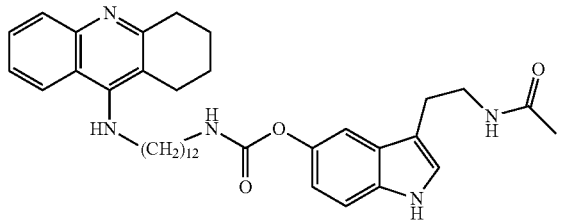

Following the same procedure as in the Example 1, but starting from compound III, where R$_1$, R$_2$=H, A=(CH$_2$)$_{12}$ (115 mg; 0.3 mmol), the 84 mg of the title compound was obtained with the yield of 89%.

$^1$H NMR (200 MHz, CDCl$_3$), δ (ppm): 8.88 (br. s, 1H, NH$_{indole}$), 7.94 (m, 2H, H$_{arom}$), 7.54 (m, 1H, H$_{arom}$), 7.34 (m, 1H, H$_{arom}$), 7.22 (m, 2H, H$_{arom}$), 6.89 (dd, J$_1$=8.6 Hz, J$_2$=2.0 Hz, 1H, H$_{arom}$), 5.80 (br. s, 1H, NHCOO), 5.20 (t, J=5.9 Hz, 1H, NHCOCH$_3$), 3.98 (br. s, 1H, NH), 3.47 (m, 4H), 3.23 (m, 2H), 3.06 (br. s, 2H), 2.82 (t, J=6.6 Hz, 2H), 2.70 (br. 2H), 1.91 (m, 7H), 1.62 (m, 4H), 1.27 (br. s, 16H); $^{13}$C NMR (50 MHz, CDCl$_3$), δ (ppm): 170.52, 158.52, 156.04, 151.11, 147.55, 144.53, 134.31, 128.68, 128.52, 127.80, 123.74, 123.66, 123.15, 120.32, 116.63, 115.88, 113.08, 111.80, 111.15, 49.71, 41.49, 39.96, 34.10, 31.96, 30.05, 29.66, 29.66, 29.66, 29.66, 29.50, 29.42, 27.08, 26.92, 25.30, 24.93, 23.47, 23.21, 22.94; HR MS EI(+)(m/z): calculated for C$_{38}$H$_{52}$N$_5$O$_3$ ([M+H]$^+$) 626.4070. found 626.4079.

Example 16

3-[2-(acetylamino)ethyl]-1H-indol-5-yl{10-[(7-chloro-1,2,3,4-tetrahydroacridin-9-yl)amino]decyl}carbamate

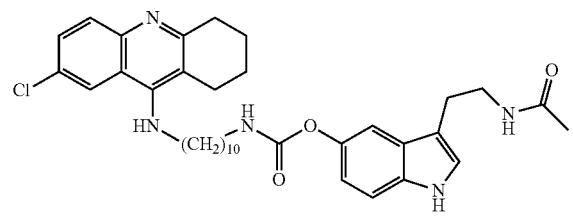

Following the same procedure as in the Example 1, but starting from compound III, where R$_1$=7-Cl, R$_2$=H, A=(CH$_2$)$_{10}$ (116 mg; 0.3 mmol), the 81 mg of the title compound was obtained with the yield of 85%.

$^1$H NMR (200 MHz, CDCl$_3$), δ (ppm): 8.66 (br. s, 1H, NH$_{indole}$), 7.94 (m, 1H, H$_{arom}$), 7.82 (m, 1H, H$_{arom}$), 7.46 (m, 1H, H$_{arom}$), 7.23 (m, 2H, H$_{arom}$), 6.92 (m, 2H, H$_{arom}$), 5.74 (br. t, 1H, NHCOO), 5.17 (t, J=5.0 Hz, 1H, NHCOCH$_3$), 3.91 (br. s, 1H, NH), 3.47 (m, 4H), 3.26 (m, 2H), 3.03 (br. s, 2H), 2.84 (t, J=7.0 Hz, 2H), 2.69 (br. s, 2H), 1.90 (m, 7H), 1.62 (m, 4H); 1.30 (br. s, 12H); $^{13}$C NMR (50 MHz, CDCl$_3$), δ (ppm): 170.46, 159.02, 155.99, 150.28, 146.16, 144.59, 134.28, 130.55, 129.21, 129.16, 127.82, 123.60, 122.37, 121.09, 116.85, 116.74, 113.22, 111.77, 111.20, 49.69, 41.48, 39.97, 34.22, 31.96, 30.05, 29.59, 29.56, 29.47, 29.38, 27.04, 26.91, 25.34, 24.88, 23.52, 23.13, 22.88; HR MS EI(+)(m/z): calculated for C$_{36}$H$_{47}$N$_5$O$_3$Cl ([M+H]$^+$) 632.3367. found 632.3380.

Example 17

3-[2-(acetylamino)ethyl]-1H-indol-5-yl{12-[(7-chloro-1,2,3,4-tetrahydroacridin-9-yl)amino]dodecyl}carbamate

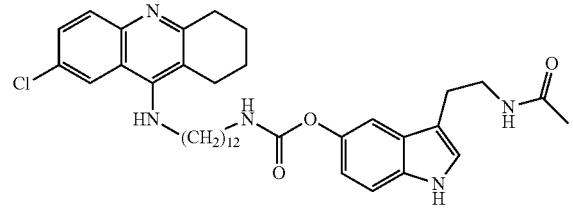

Following the same procedure as in the Example 1, but starting from compound III, where R$_1$=7-Cl, R$_2$=H, A=(CH$_2$)$_{12}$ (138 mg; 0.33 mmol), the 88 mg of the title compound was obtained with the yield of 80%.

$^1$H NMR (200 MHz, CDCl$_3$), δ (ppm): 8.65 (br. s, 1H, NH$_{indole}$), 7.94 (d, J=2.0 Hz, 1H, H$_{arom}$), 7.82 (d, J=9.0 Hz, 1H, H$_{arom}$), 7.47 (dd, J$_1$=9.2 Hz, J$_2$=2.2 Hz, 1H, H$_{arom}$), 7.24 (m, 2H, H$_{arom}$), 6.92 (m, 2H, H$_{arom}$), 5.72 (br. s, 1H, NHCOO), 5.14 (br. t, J=5.7 Hz, 1H, NHCOCH$_3$), 3.90 (br. s, 1H, NH), 3.48 (m, 4H), 3.27 (m, 2H), 3.03 (br. s, 2H), 2.85 (t, J=6.6 Hz, 2H), 2.69 (br. s, 2H), 1.90 (m, 7H), 1.62 (m, 4H), 1.28 (br. s, 16H); $^{13}$C NMR (50 MHz, CDCl$_3$), δ (ppm): 170.44, 159.00, 155.96, 150.28, 146.15, 144.60, 134.28, 130.55, 129.20, 129.17, 127.83, 123.58, 122.37, 121.08, 116.82, 116.76, 113.26, 111.75, 111.21, 49.72, 41.51, 39.97, 34.22, 31.98, 30.08, 29.68, 29.68, 29.63, 29.51, 29.45, 28.29, 27.07, 26.96, 25.35, 24.88, 23.53, 23.13, 22.88; HR MS EI(+) (m/z): calculated for C$_{38}$H$_{51}$N$_5$O$_3$Cl ([M+H]) 660.3680. found 660.3691.

Example 18

3-[2-(acetylamino)ethyl]-1H-indol-5-yl{10-[(6-chloro-1,2,3,4-tetrahydroacridin-9-yl)amino]decyl}carbamate

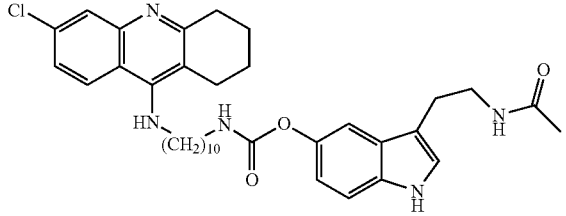

Following the same procedure as in the Example 1, but starting from compound III, where R$_1$=6-Cl, R$_2$=H, A=(CH$_2$)$_{10}$ (163 mg; 0.42 mmol), the 81 mg of the title compound was obtained with the yield of 61%.

$^1$H NMR (200 MHz, CDCl$_3$), δ (ppm): 8.74 (br. s, 1H, NH$_{indole}$), 7.90 (m, 2H, H$_{arom}$), 7.26 (m, 2H, H$_{arom}$), 7.22 (m, 1H, H$_{arom}$), 6.90 (m, 2H, H$_{arom}$), 5.77 (br. s, 1H, NHCOO), 5.22 (t, J=5.6 Hz, 1H, NHCOCH$_3$), 3.98 (br. s, 1H, NH), 3.47 (m, 4H), 3.26 (m, 2H), 3.02 (m, 2H), 2.82 (t, J=6.8 Hz, 2H), 2.66 (br. s, 2H), 1.89 (m, 7H), 1.61 (m, 4H), 1.29 (br. s, 12H); $^{13}$C NMR (50 MHz, CDCl$_3$), δ (ppm): 170.52, 159.74, 156.05, 151.07, 148.38, 144.56, 134.29, 134.12, 127.82, 127.68, 124.89, 124.33, 123.63, 118.58, 116.67, 115.85, 113.15, 111.78, 111.17, 49.79, 41.46, 39.96, 34.21, 31.96, 30.03, 29.56, 29.55, 29.45, 29.36, 27.02, 26.88, 25.31, 24.74, 23.49, 23.11, 22.84; HR MS EI(+)(m/z): calculated for C$_{36}$H$_{46}$N$_5$O$_3$ClNa ([M+Na]$^+$) 654.3187. found 654.3185.

Example 19

3-[2-(acetylamino)ethyl]-1H-indol-5-yl{12-[(6-chloro-1,2,3,4-tetrahydroacridin-9-yl)amino]dodecyl}carbamate

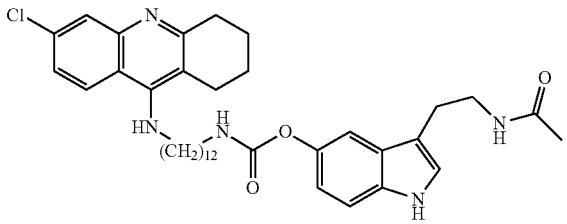

Following the same procedure as in the Example 1, but starting from compound III, where R$_1$=6-Cl, R$_2$=H, A=(CH$_2$)$_{12}$ (104 mg; 0.25 mmol), the 59 mg of the title compound was obtained with the yield of 72%.

$^1$H NMR (200 MHz, CDCl$_3$), δ (ppm): 8.29 (br. s, 1H, NH$_{indole}$), 7.90 (m, 1H, H$_{arom}$), 7.29 (m, 2H, H$_{arom}$), 7.25 (m, 2H, H$_{arom}$), 6.97 (m, 2H, H$_{arom}$), 5.61 (br. s, 1H, NHCOO), 5.08 (br. t, J=7.2 Hz, 1H, NHCOCH$_3$), 3.96 (br. s, 1H, NH), 3.52 (m, 4H), 3.27 (m, 2H), 3.02 (m, 2H), 2.89 (t, J=6.6 Hz, 2H), 2.66 (br. s, 2H), 1.92 (m, 7H), 1.62 (m, 4H), 1.27 (br. s, 16H); $^{13}$C NMR (50 MHz, CDCl$_3$), δ (ppm): 170.45, 163.52, 158.35, 150.70, 147.42, 144.75, 134.30, 134.27, 127.86, 127.76, 124.88, 124.38, 123.53, 120.63, 118.60, 116.94, 113.51, 111.74, 111.33, 49.85, 41.49, 39.99, 34.24, 31.99, 30.09, 29.67, 29.61, 29.58, 29.50, 29.44, 29.13, 27.08, 26.94, 25.40, 24.76, 23.58, 23.15, 22.87; HR MS EI(+)(m/z): calculated for C$_{38}$H$_{51}$N$_5$O$_3$Cl ([M+H]$^+$) 660.3680. found 660.3674.

The invention is further described by the following numbered paragraphs:

1. Cholinesterase inhibitors of general formula (I),

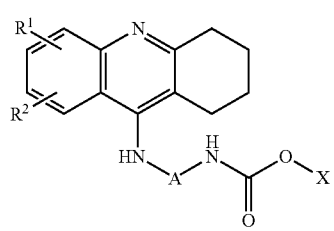

wherein

A represents straight or branched C$_2$-C$_{14}$-alkyl group,

R$^1$, R$^2$ are the same or different and they are independently selected from hydrogen, halogen atom, C$_1$-C$_3$-alkyl, C$_1$-C$_3$-alkyl substituted by halogen atom and C$_1$-C$_3$-alkoxy, X represents a radical of formula (A) or (B):

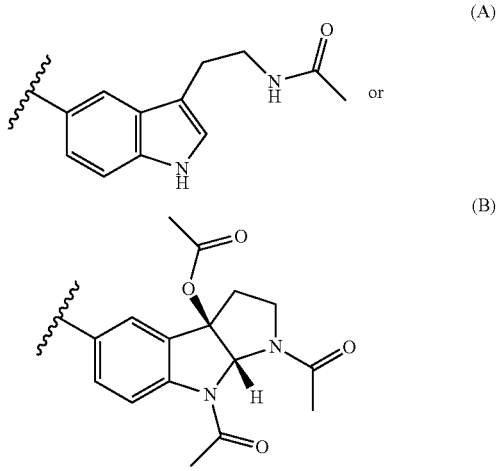

and the pharmaceutically acceptable salts thereof.

2. Cholinesterase inhibitors according to paragraph 1 of formula (I), wherein X represent group (A), A is C$_2$-C$_{14}$-alkyl and both R$^1$ and R$^2$ represent hydrogen atoms.

3. Cholinesterase inhibitors according to paragraph 1 of formula (I), in which X represent group (A), A is C$_2$-C$_{14}$-alkyl, R$^1$ represents a halogen atom substituted at position 6 or 7 of 1,2,3,4-tetrahydroacridine ring, and R$^2$ represents a hydrogen atom.

4. Cholinesterase inhibitors according to paragraph 3 of formula (I), in which $R^1$ represents a chloride atom substituted at position 6 or 7 of 1,2,3,4-tetrahydroacridine ring, and the remaining substituents are as defined in paragraph 3.

5. Cholinesterase inhibitors according to paragraph 1 of formula (I), wherein X represents group (B), A is $C_2$-$C_{14}$-alkyl, and both $R^1$ and $R^2$ represent hydrogen atoms.

6. Cholinesterase inhibitors according to paragraph 1 selected from the group comprising:
3-[2-(acetylamino)ethyl]-1H-indol-5-yl[7-(1,2,3,4-tetrahydroacridin-9-ylamino)heptyl]carbamate,
3-[2-(acetylamino)ethyl]-1H-indol-5-yl[2-(1,2,3,4-tetrahydroacridin-9-ylamino)ethyl]carbamate,
3-[2-(acetylamino)ethyl]-1H-indol-5-yl[6-(1,2,3,4-tetrahydroacridin-9-ylamino)hexyl]carbamate,
3-[2-(acetylamino)ethyl]-1H-indol-5-yl{7-[(6-chloro-1,2,3,4-tetrahydroacridin-9-yl)amino]heptyl}carbamate,
3-[2-(acetylamino)ethyl]-1H-indol-5-yl{2-[(6-chloro-1,2,3,4-tetrahydroacridin-9-yl)amino]ethyl}carbamate,
1,8-diacetyl-5-({[7-(1,2,3,4-tetrahydroacridin-9-ylamino)heptyl]carbamoyl}oxy)-2,3,8,8a-tetrahydropyrrolo[2,3-b]indol-3a(1H)-yl acetate,
1,8-diacetyl-5-({[6-(1,2,3,4-tetrahydroacridin-9-ylamino)hexyl]carbamoyl}oxy)-2,3,8,8a-tetrahydropyrrolo[2,3-b]indol-3a(1H)-yl acetate,
3-[2-(acetylamino)ethyl]-1H-indol-5-yl[3-(1,2,3,4-tetrahydroacridin-9-ylamino)propyl]carbamate,
3-[2-(acetylamino)ethyl]-1H-indol-5-yl[4-(1,2,3,4-tetrahydroacridin-9-ylamino)butyl]carbamate,
3-[2-(acetylamino)ethyl]-1H-indol-5-yl[5-(1,2,3,4-tetrahydroacridin-9-ylamino)pentyl]carbamate,
3-[2-(acetylamino)ethyl]-1H-indol-5-yl[8-(1,2,3,4-tetrahydroacridin-9-ylamino)octyl]carbamate,
3-[2-(acetylamino)ethyl]-1H-indol-5-yl{7-[(7-chloro-1,2,3,4-tetrahydroacridin-9-yl)amino]heptyl}carbamate,
3-[2-(acetylamino)ethyl]-1H-indol-5-yl{2-[(7-chloro-1,2,3,4-tetrahydroacridin-9-yl)amino]ethyl}carbamate,
3-[2-(acetylamino)ethyl]-1H-indol-5-yl[10-(1,2,3,4-tetrahydroacridin-9-ylamino)decyl]carbamate,
3-[2-(acetylamino)ethyl]-1H-indol-5-yl[12-(1,2,3,4-tetrahydroacridin-9-ylamino)dodecyl]carbamate,
3-[2-(acetylamino)ethyl]-1H-indol-5-yl{10-[(7-chloro-1,2,3,4-tetrahydroacridin-9-yl)amino]decyl}carbamate,
3-[2-(acetylamino)ethyl]-1H-indol-5-yl{12-[(7-chloro-1,2,3,4-tetrahydroacridin-9-yl)amino]dodecyl}carbamate,
3-[2-(acetylamino)ethyl]-1H-indol-5-yl{10-[(6-chloro-1,2,3,4-tetrahydroacridin-9-yl)amino]decyl}carbamate,
3-[2-(acetylamino)ethyl]-1H-indol-5-yl{12-[(6-chloro-1,2,3,4-tetrahydroacridin-9-yl)amino]dodecyl}carbamate.

7. The use of cholinesterases inhibitors of formula (I),

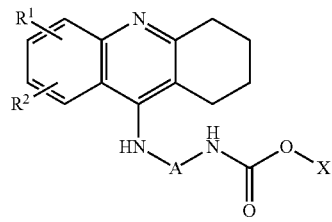

(I)

wherein
A represents straight or branched $C_2$-$C_{14}$-alkyl group,
$R^1$, $R^2$ are the same or different and they are independently selected from hydrogen, halogen, $C_1$-$C_3$-alkyl, $C_1$-$C_3$-alkyl substituted by halogen atoms and $C_1$-$C_3$-alkoxy,
X represents a radical of formula (A) or (B):

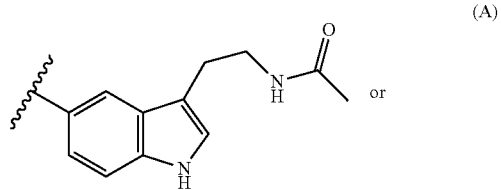

(A)

or

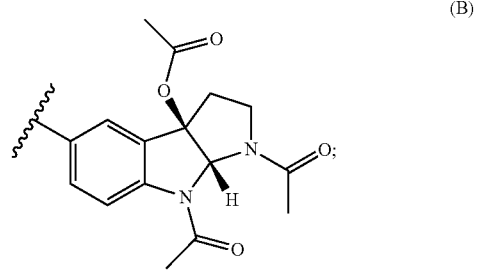

(B)

and the pharmaceutically acceptable salts thereof for the preparation of a medicament for prevention and/or treatment of neurodegenerative disorders.

8. The use according to paragraph 7, in which neurodegenerative disorders include: senile dementia, vascular dementia, mild cognitive impairment, attention deficit disorder, neurodegenerative dementia with abnormal protein aggregation, in particular Alzheimer's disease, Parkinson's disease, ALS or prion diseases like Creutzfeldt-Jakob disease, and Gerstmann-Strässler-Scheinker disease.

9. The pharmaceutical formulation which contains as the active substance hybrid cholinesterase inhibitor represented by general formula (I)

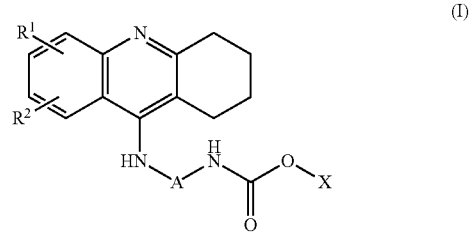

(I)

wherein
A represents straight or branched $C_2$-$C_{14}$-alkyl group,
$R^1$, $R^2$ are the same or different and they are independently selected from hydrogen, halogen, $C_1$-$C_3$-alkyl, $C_1$-$C_3$-alkyl substituted by halogen atoms and $C_1$-$C_3$-alkoxy,
X represents a radical of formula (A) or (B):

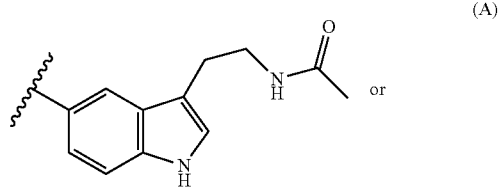

(A)

or or the pharmaceutically acceptable salt thereof and pharmaceutically acceptable carriers and/or excipients.

10. The process for preparation of cholinesterase inhibitors of general formula (I),

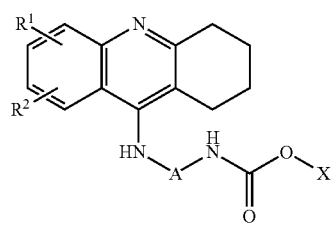
(I)

wherein
A represents straight or branched $C_2$-$C_{14}$-alkyl group,
$R^1$, $R^2$ are the same or different and they are independently selected from hydrogen, halogen, $C_1$-$C_3$-alkyl, $C_1$-$C_3$-alkyl substituted by halogen atoms and $C_1$-$C_3$-alkoxy,
X represents a radical of formula (A) or (B):

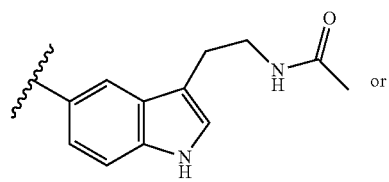
(A)

or

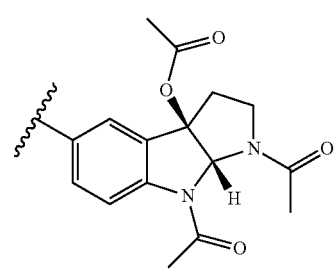
(B)

characterized in that the amino derivative of 1,2,3,4-tetrahydroacridine of formula (III)

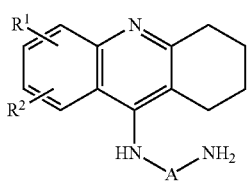
(III)

in which A, $R^1$ and $R^2$ have the same meaning as in formula (I), is subject to N-acylation reaction with an active ester derivative of melatonin or its oxidation product, preferably 4-nitrophenyl carbonate derivative of formula (II)

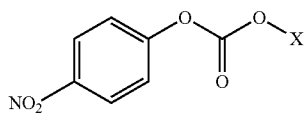
(II)

in which X has the same meaning as in formula (I).

11. New compounds which are 4-nitrophenyl carbonate derivatives of formula (II),

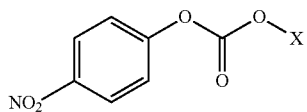
(II)

in which X represents a radical of formula (A) or (B):

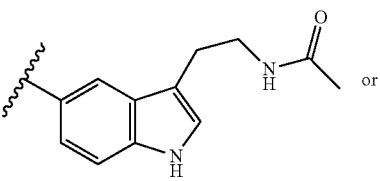
(A)

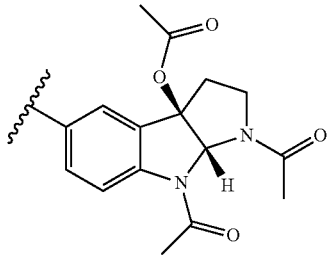
(B)

12. A method of treatment of neurodegenerative disorders comprising administration of the therapeutically effective amount of a compound of general formula (I),

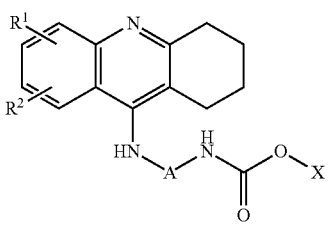
(I)

wherein
A represents straight or branched $C_2$-$C_{14}$-alkyl group,
$R^1$, $R^2$ are the same or different and they are independently selected from hydrogen, halogen, $C_1$-$C_3$-alkyl, $C_1$-$C_3$-alkyl substituted by halogen atoms and $C_1$-$C_3$-alkoxy, X represents a radical of formula (A) or (B):

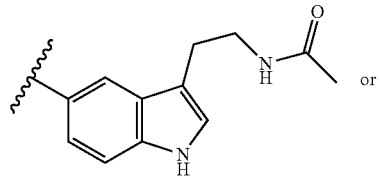
(A)

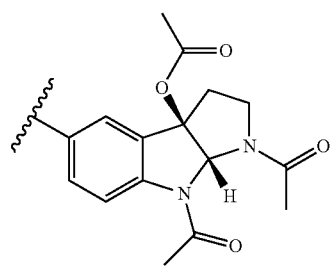
(B)

or its pharmaceutical formulation or its unit dosage form to a patient in a need of such treatment.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. Cholinesterase inhibitors of general formula (I),

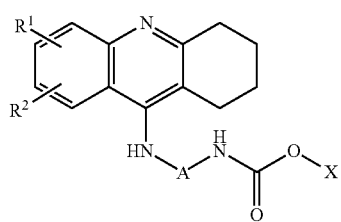
(I)

wherein

A represents straight or branched $C_2$-$C_{14}$-alkyl group, $R^1$, $R^2$ are the same or different and they are independently selected from hydrogen, halogen atom, $C_1$-$C_3$-alkyl, $C_1$-$C_3$-alkyl substituted by halogen atom and $C_1$-$C_3$-alkoxy, X represents a radical of formula (A) or (B):

(A)

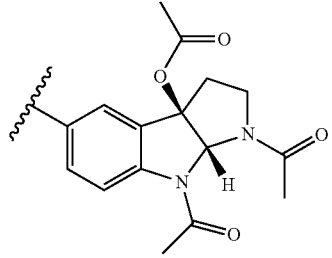
(B)

and the pharmaceutically acceptable salts thereof.

2. Cholinesterase inhibitors according to claim 1 of formula (I), wherein X represent group (A), A is $C_2$-$C_{14}$-alkyl and both $R^1$ and $R^2$ represent hydrogen atoms.

3. Cholinesterase inhibitors according to claim 1 of formula (I), in which X represent group (A), A is $C_2$-$C_{14}$-alkyl, $R^1$ represents a halogen atom substituted at position 6 or 7 of 1,2,3,4-tetrahydroacridine ring, and $R^2$ represents a hydrogen atom.

4. Cholinesterase inhibitors according to claim 3 of formula (I), in which $R^1$ represents a chloride atom substituted at position 6 or 7 of 1,2,3,4-tetrahydroacridine ring, and the remaining substituents are as defined in claim 3.

5. Cholinesterase inhibitors according to claim 1 of formula (I), wherein X represents group (B), A is $C_2$-$C_{14}$-alkyl, and both $R^1$ and $R^2$ represent hydrogen atoms.

6. Cholinesterase inhibitors according to claim 1 selected from the group comprising:
   3-[2-(acetylamino)ethyl]-1H-indol-5-yl[7-(1,2,3,4-tetrahydroacridin-9-ylamino)heptyl]carbamate,
   3-[2-(acetylamino)ethyl]-1H-indol-5-yl[2-(1,2,3,4-tetrahydroacridin-9-ylamino)ethyl]carbamate,
   3-[2-(acetylamino)ethyl]-1H-indol-5-yl[6-(1,2,3,4-tetrahydroacridin-9-ylamino)hexyl]carbamate,
   3-[2-(acetylamino)ethyl]-1H-indol-5-yl{7-[(6-chloro-1,2,3,4-tetrahydroacridin-9-yl)amino]heptyl}carbamate,
   3-[2-(acetylamino)ethyl]-1H-indol-5-yl{2-[(6-chloro-1,2,3,4-tetrahydroacridin-9-yl)amino]ethyl}carbamate,
   1,8-diacetyl-5-({[7-(1,2,3,4-tetrahydroacridin-9-ylamino)heptyl]carbamoyl}oxy)-2,3,8,8a-tetrahydropyrrolo[2,3-b]indol-3a(1H)-yl acetate,
   1,8-diacetyl-5-({[6-(1,2,3,4-tetrahydroacridin-9-ylamino)hexyl]carbamoyl}oxy)-2,3,8,8a-tetrahydropyrrolo[2,3-b]indol-3a(1H)-yl acetate,
   3-[2-(acetylamino)ethyl]-1H-indol-5-yl[3-(1,2,3,4-tetrahydroacridin-9-ylamino)propyl]carbamate,
   3-[2-(acetylamino)ethyl]-1H-indol-5-yl[4-(1,2,3,4-tetrahydroacridin-9-ylamino)butyl]carbamate,
   3-[2-(acetylamino)ethyl]-1H-indol-5-yl[5-(1,2,3,4-tetrahydroacridin-9-ylamino)pentyl]carbamate,
   3-[2-(acetylamino)ethyl]-1H-indol-5-yl[8-(1,2,3,4-tetrahydroacridin-9-ylamino)octyl]carbamate,
   3-[2-(acetylamino)ethyl]-1H-indol-5-yl{7-[(7-chloro-1,2,3,4-tetrahydroacridin-9-yl)amino]heptyl}carbamate,
   3-[2-(acetylamino)ethyl]-1H-indol-5-yl{2-[(7-chloro-1,2,3,4-tetrahydroacridin-9-yl)amino]ethyl}carbamate,
   3-[2-(acetylamino)ethyl]-1H-indol-5-yl[10-(1,2,3,4-tetrahydroacridin-9-ylamino)decyl]carbamate,
   3-[2-(acetylamino)ethyl]-1H-indol-5-yl[12-(1,2,3,4-tetrahydroacridin-9-ylamino)dodecyl]carbamate,
   3-[2-(acetylamino)ethyl]-1H-indol-5-yl{10-[(7-chloro-1,2,3,4-tetrahydroacridin-9-yl)amino]decyl}carbamate, 3-[2-(acetylamino)ethyl]-1H-indol-5-yl{12-[(7-chloro-1,2,3,4-tetrahydroacridin-9-yl)amino]dodecyl}carbamate, 3-[2-(acetylamino)ethyl]-1H-indol-5-yl{10-[(6-chloro-1,2,3,4-tetrahydroacridin-9-yl)amino]decyl}carbamate, 3-[2-(acetylamino)ethyl]-1H-indol-5-yl{12-[(6-chloro-1,2,3,4-tetrahydroacridin-9-yl)amino]dodecyl}carbamate.

7. A pharmaceutical formulation which contains as the active substance hybrid cholinesterase inhibitor of claim 1 or the pharmaceutically acceptable salt thereof and pharmaceutically acceptable carriers and/or excipients.

\* \* \* \* \*